US010172968B2

(12) United States Patent
Shur et al.

(10) Patent No.: US 10,172,968 B2
(45) Date of Patent: Jan. 8, 2019

(54) STORAGE DEVICE INCLUDING TARGET UV ILLUMINATION RANGES

(71) Applicant: Sensor Electronic Technology, Inc., Columbia, SC (US)

(72) Inventors: Michael Shur, Latham, NY (US); Maxim S. Shatalov, Columbia, SC (US); Timothy James Bettles, Irmo, SC (US); Yuri Bilenko, Columbia, SC (US); Saulius Smetona, Concord, NC (US); Alexander Dobrinsky, Loudonville, NY (US); Remigijus Gaska, Columbia, SC (US)

(73) Assignee: Sensor Electronic Technology, Inc., Columbia, SC (US)

(*) Notice: Subject to any disclaimer, the term of this patent is extended or adjusted under 35 U.S.C. 154(b) by 0 days.

(21) Appl. No.: 15/670,750

(22) Filed: Aug. 7, 2017

(65) Prior Publication Data
US 2017/0333583 A1 Nov. 23, 2017

Related U.S. Application Data

(63) Continuation of application No. 14/541,245, filed on Nov. 14, 2014, now Pat. No. 9,724,441, which is a (Continued)

(51) Int. Cl.
*A61L 2/10* (2006.01)
*A23L 3/28* (2006.01)
*F25D 17/04* (2006.01)

(52) U.S. Cl.
CPC .............. *A61L 2/10* (2013.01); *A23L 3/28* (2013.01); *F25D 17/042* (2013.01);
(Continued)

(58) Field of Classification Search
CPC .... A61L 2/10; A61L 2202/14; A61L 2202/21; A61L 2202/20; F21V 9/06; F25D 17/042; F25D 2317/0417
See application file for complete search history.

(56) References Cited

U.S. PATENT DOCUMENTS 2,482,507 A  9/1949 Rentschler et al.
3,817,703 A  6/1974 Atwood
(Continued)

FOREIGN PATENT DOCUMENTS

CN  1269246 A  10/2000
CN  2488020 Y  4/2002
(Continued)

OTHER PUBLICATIONS

Zhou, Z., Application No. 201380053729.9, Office Action2 (with English translation), dated Jan. 29, 2018, 13 pages.
(Continued)

*Primary Examiner* — Elizabeth Martin
(74) *Attorney, Agent, or Firm* — LaBatt, LLC

(57) ABSTRACT

Ultraviolet radiation is directed within a storage area formed of a plurality of layers including an outer ultraviolet reflective layer, an inner ultraviolet transparent layer, and a layer located between the outer ultraviolet reflective layer and the inner ultraviolet transparent layer. The refractive index of the layer between the outer ultraviolet reflective layer and the inner ultraviolet transparent layer is less than the refractive index of the inner ultraviolet transparent layer. A set of ultraviolet radiation sources generate ultraviolet radiation directed at a set of items located within the storage area.

20 Claims, 11 Drawing Sheets

Related U.S. Application Data continuation-in-part of application No. 14/012,667, filed on Aug. 28, 2013, now Pat. No. 9,795,699.

(60) Provisional application No. 61/904,119, filed on Nov. 14, 2013, provisional application No. 61/989,891, filed on May 7, 2014, provisional application No. 61/694,232, filed on Aug. 28, 2012, provisional application No. 61/694,229, filed on Aug. 28, 2012.

(52) U.S. Cl.
CPC ....... *A61L 2202/14* (2013.01); *A61L 2202/21* (2013.01); *F25D 2317/0417* (2013.01)

(56) References Cited

U.S. PATENT DOCUMENTS

| | | |
|---|---|---|
| 4,736,416 A | 4/1988 | Weinert |
| 4,857,277 A | 8/1989 | Broomfield |
| 4,867,052 A | 9/1989 | Cipelletti |
| 5,078,971 A | 1/1992 | Matuda et al. |
| 5,117,642 A | 6/1992 | Nakanishi et al. |
| 5,136,170 A | 8/1992 | Gellert |
| 5,230,220 A | 7/1993 | Kang et al. |
| 5,364,645 A | 11/1994 | Lagunas-Solar et al. |
| 5,454,944 A | 10/1995 | Clack |
| 5,768,898 A | 6/1998 | Seok et al. |
| 5,836,669 A | 11/1998 | Hed |
| 5,865,959 A | 2/1999 | Meinzer et al. |
| 5,889,684 A | 3/1999 | Ben-David et al. |
| 5,901,564 A | 5/1999 | Comeau, II |
| 5,919,422 A | 7/1999 | Yamanaka et al. |
| 6,165,526 A | 12/2000 | Newman |
| 6,182,453 B1 | 2/2001 | Forsberg |
| 6,312,608 B1 | 11/2001 | Buckner |
| 6,447,721 B1 | 9/2002 | Horton, III et al. |
| 6,471,136 B1 | 10/2002 | Chatterjee et al. |
| 6,477,853 B1 | 11/2002 | Khorram |
| 6,524,529 B1 | 2/2003 | Horton, III |
| 6,565,803 B1 | 5/2003 | Bolton et al. |
| 6,574,984 B1 | 6/2003 | McCrea et al. |
| 6,576,188 B1 | 6/2003 | Rose et al. |
| 6,579,495 B1 | 6/2003 | Maiden |
| 6,592,816 B1 | 7/2003 | Ebel et al. |
| 6,673,137 B1 | 1/2004 | Wen |
| 6,735,479 B2 | 5/2004 | Fabian et al. |
| 6,818,177 B1 | 11/2004 | Turcotte |
| 6,878,761 B2 | 4/2005 | Gugumus |
| 7,026,018 B2 | 4/2006 | Kranovich |
| 7,160,370 B2 | 1/2007 | Baca et al. |
| 7,296,422 B2 | 11/2007 | Strohm et al. |
| 7,323,065 B2 | 1/2008 | Fencl et al. |
| 7,401,469 B2 | 7/2008 | Joshi et al. |
| 7,452,561 B2 | 11/2008 | Newman |
| 7,634,996 B2 | 12/2009 | Gaska et al. |
| 7,645,381 B2 | 1/2010 | Oranski et al. |
| 7,754,156 B2 | 7/2010 | Hyde et al. |
| 7,897,104 B2 | 3/2011 | Kwon |
| 8,062,589 B2 | 11/2011 | Naarup |
| 8,114,342 B2 | 2/2012 | Jung et al. |
| 8,178,042 B2 | 5/2012 | Jung et al. |
| 8,277,734 B2 | 10/2012 | Koudymov et al. |
| 8,384,047 B2 | 2/2013 | Shur et al. |
| 8,828,315 B2 | 9/2014 | Ryska et al. |
| 9,006,680 B2 | 4/2015 | Bettles et al. |
| 9,042,967 B2 | 5/2015 | Dacosta et al. |
| 9,061,082 B2 | 6/2015 | Gaska et al. |
| 9,138,499 B2 | 9/2015 | Bettles et al. |
| 9,179,703 B2 | 11/2015 | Shur et al. |
| 9,572,903 B2 | 2/2017 | Dobrinsky et al. |
| 9,603,960 B2 | 3/2017 | Dobrinsky et al. |
| 9,687,577 B2 | 6/2017 | Dobrinsky et al. |
| 9,878,061 B2 | 1/2018 | Shur et al. |
| 2002/0063954 A1 | 5/2002 | Horton, III |
| 2002/0074559 A1 | 6/2002 | Dowling et al. |
| 2002/0122743 A1 | 9/2002 | Huang |
| 2002/0176809 A1 | 11/2002 | Siess |
| 2003/0019222 A1 | 1/2003 | Takahashi et al. |
| 2003/0019505 A1 | 1/2003 | Scheir et al. |
| 2003/0164754 A1 | 9/2003 | Roseen |
| 2003/0194692 A1 | 10/2003 | Purdum |
| 2004/0018125 A1 | 1/2004 | Yang et al. |
| 2004/0210099 A1 | 10/2004 | Shiratori |
| 2005/0165499 A1 | 7/2005 | Stein |
| 2005/0178977 A1 | 8/2005 | Koenck et al. |
| 2005/0186124 A1 | 8/2005 | Fink et al. |
| 2005/0217282 A1 | 10/2005 | Strohm et al. |
| 2005/0257827 A1 | 11/2005 | Gaudiana et al. |
| 2005/0274965 A1 | 12/2005 | Phillips et al. |
| 2006/0091310 A1 | 5/2006 | Furry |
| 2006/0130498 A1 | 6/2006 | Joshi et al. |
| 2006/0147339 A1 | 7/2006 | Hunter et al. |
| 2006/0163169 A1 | 7/2006 | Eckhardt et al. |
| 2006/0216193 A1 | 9/2006 | Johnson et al. |
| 2006/0237687 A1 | 10/2006 | Yue et al. |
| 2007/0051901 A1 | 3/2007 | Hopaluk et al. |
| 2007/0104841 A1 | 5/2007 | Min et al. |
| 2007/0164232 A1 | 7/2007 | Rolleri et al. |
| 2007/0172560 A1 | 7/2007 | Mirtsching et al. |
| 2007/0172661 A1 | 7/2007 | Fechner et al. |
| 2007/0196235 A1 | 8/2007 | Shur et al. |
| 2007/0205382 A1 | 9/2007 | Gaska et al. |
| 2007/0248487 A1 | 10/2007 | Kay et al. |
| 2007/0295203 A1 | 12/2007 | Shekarriz et al. |
| 2008/0061005 A1 | 3/2008 | Hopaluk et al. |
| 2008/0067418 A1 | 3/2008 | Ross |
| 2008/0168788 A1 | 7/2008 | Hurlebaus et al. |
| 2008/0168790 A1 | 7/2008 | Hurlebaus et al. |
| 2008/0213129 A1 | 9/2008 | van der Pol et al. |
| 2008/0286146 A1 | 11/2008 | Schroll et al. |
| 2008/0295033 A1 | 11/2008 | Lee et al. |
| 2008/0307818 A1 | 12/2008 | Min et al. |
| 2009/0110933 A1 | 4/2009 | Hyde et al. |
| 2009/0185960 A1 | 7/2009 | Busujima |
| 2009/0228155 A1 | 9/2009 | Slifkin et al. |
| 2009/0229287 A1 | 9/2009 | Prentner |
| 2009/0280035 A1 | 11/2009 | Koudymov et al. |
| 2010/0065632 A1 | 3/2010 | Babcock et al. |
| 2010/0097013 A1 | 4/2010 | Inskeep |
| 2010/0101432 A1 | 4/2010 | Biotti et al. |
| 2010/0227031 A1 | 9/2010 | Vasilenko |
| 2010/0296971 A1 | 11/2010 | Gaska et al. |
| 2010/0307973 A1 | 12/2010 | Grcevic |
| 2011/0030560 A1 | 2/2011 | Bohlen et al. |
| 2011/0044848 A1 | 2/2011 | Wright |
| 2011/0147617 A1 | 6/2011 | Shur et al. |
| 2011/0163046 A1 | 7/2011 | Neal et al. |
| 2011/0228534 A1 | 9/2011 | Zhang et al. |
| 2011/0297241 A1 | 12/2011 | Biotti et al. |
| 2011/0306262 A1 | 12/2011 | Aprin |
| 2012/0011874 A1 | 1/2012 | Conradt et al. |
| 2012/0017628 A1 | 1/2012 | Okabe et al. |
| 2012/0025104 A1 | 2/2012 | Park et al. |
| 2012/0051030 A1 | 3/2012 | Johnson |
| 2012/0085116 A1* | 4/2012 | Maeng .................. F25D 17/042 62/264 |
| 2012/0104021 A1 | 5/2012 | Cur et al. |
| 2012/0126134 A1 | 5/2012 | Deal et al. |
| 2013/0015753 A1 | 1/2013 | Son et al. |
| 2013/0048545 A1 | 2/2013 | Shatalov et al. |
| 2013/0337121 A1 | 12/2013 | Sugano et al. |
| 2014/0042012 A1 | 2/2014 | Clement et al. |
| 2014/0060094 A1 | 3/2014 | Shur et al. |
| 2014/0060095 A1 | 3/2014 | Shur et al. |
| 2014/0060096 A1 | 3/2014 | Shur et al. |
| 2014/0060104 A1 | 3/2014 | Shur et al. |
| 2014/0102127 A1 | 4/2014 | Yum et al. |
| 2014/0202962 A1 | 7/2014 | Bilenko et al. |
| 2014/0209928 A1 | 7/2014 | Teng et al. |
| 2015/0008167 A1 | 1/2015 | Shturm et al. |
| 2015/0069270 A1 | 3/2015 | Shur et al. |
| 2015/0161909 A1 | 6/2015 | Won et al. |
| 2015/0165079 A1 | 6/2015 | Shur et al. |
| 2015/0217011 A1 | 8/2015 | Bettles et al. |

(56) References Cited

U.S. PATENT DOCUMENTS

| | | | |
|---|---|---|---|
| 2015/0297767 | A1 | 10/2015 | Gaska et al. |
| 2015/0336810 | A1 | 11/2015 | Smetona et al. |
| 2016/0000953 | A1 | 1/2016 | Bettles et al. |
| 2016/0058020 | A1 | 3/2016 | Shur et al. |
| 2016/0114186 | A1 | 4/2016 | Dobrinsky et al. |
| 2016/0128526 | A1 | 5/2016 | Dobrinsky et al. |
| 2016/0324996 | A1 | 11/2016 | Bilenko et al. |
| 2017/0057842 | A1 | 3/2017 | Dobrinsky et al. |
| 2017/0071332 | A1 | 3/2017 | Herring et al. |
| 2017/0100494 | A1 | 4/2017 | Dobrinsky et al. |
| 2017/0100495 | A1 | 4/2017 | Shur et al. |
| 2017/0100496 | A1 | 4/2017 | Shur et al. |
| 2017/0157276 | A1 | 6/2017 | Dobrinsky et al. |
| 2017/0189711 | A1 | 7/2017 | Shur et al. |
| 2017/0197002 | A1 | 7/2017 | Dobrinsky et al. |
| 2017/0245527 | A1 | 8/2017 | Dobrinsky et al. |
| 2017/0245616 | A1 | 8/2017 | Lakios et al. |
| 2017/0281812 | A1 | 10/2017 | Dobrinsky et al. |
| 2018/0243458 | A1 | 8/2018 | Shatalov et al. |

FOREIGN PATENT DOCUMENTS

| | | | |
|---|---|---|---|
| CN | 101171938 | A | 5/2008 |
| CN | 101322000 | A | 12/2008 |
| CN | 102389579 | A | 3/2012 |
| CN | 102564003 | A | 7/2012 |
| EP | 1038536 | B1 | 6/2005 |
| JP | 2002204653 | A | 7/2002 |
| KR | 1020090074966 | A | 7/2009 |
| KR | 1020110057773 | A | 6/2011 |
| KR | 1020120011458 | A | 2/2012 |
| WO | 2013096243 | A1 | 6/2013 |

OTHER PUBLICATIONS

Cox, A., U.S. Appl. No. 14/012,637, Notice of Allowance, dated Jan. 19, 2018, 43 pages.

果品蔬菜保鲜技术和设备 (Google translation of title: "Fruit and vegetable preservation technology and equipment"), Received Mar. 14, 2017, 2 pages. (English translation is not available).

Bialka et al., "Decontamination of *Escherichia coli* O157:H7 and *Salmonella enterica* on Blueberries Using Ozone and Pulsed UV-Light," Journal of Food Science, 2007, 7 pages, vol. 72, No. 9.

Bialka et al., "Modeling the inactivation of *Escherichia coli* O157:H7 and *Salmonella enterica* on raspberries and strawberries resulting from exposure to ozone or pulsed UV-light," Journal of Food Engineering, 2008, 6 pages, vol. 85.

Bialka et al., "Pulsed UV-light Penetration of Characterization and the Inactivation of *Escherichia coli* K12 in Solid Model Systems," Abstract, American Society of Agricultural and Biological Engineers, 2013, 1 page.

Bialka et al., "Efficacy of Pulsed UV-Light for the Decontamination of *Escherichia coli* O157:H7 and *Salmonella* spp. on Raspberries and Strawberries," Journal of Food Science, 2008, 7 pages, vol. 73, No. 5.

Chang et al., "Removal of Ethylene and Secondary Organic Aerosols Using UV-C 254+185 with TiO2 Catalyst," Aerosol and Air Quality Research, 2013, 9 pages.

Cheba et al., "Inactivation of *E. coli* cell viability and DNA Photo-breakage by Pulsed Nitrogen Laser Radiation," American Institute of Physics, 2005, 5 pages.

Chisari et al., "Improving the quality of fresh-cut melon through inactivation of degradative oxidase and pectinase enzymatic activities by UV-C treatment," Institute of Food Science and Technology, 2011, 6 pages.

Demirci et al., "Disinfection of water by flow-through a Pulsed UV Light Sterilization System," Abstract, Ultrapure Water Journal, 2000, 1 page.

Demirci et al., "Pulsed Ultraviolet Light," Sage Publications, 2008, 5 pages.

Hillegas et al., "Inactivation of Clostridium sporogenes in Clover Honey by Pulsed UV-light Treatment," Abstract, American Society of Agricultural and Biological Engineers, 2013, 1 page.

Jun et al., "Pulsed UV-light treatment of corn meal for inactivation of Aspergillus niger spores," International Journal of Food Science and Technology, 2003, 6 pages.

Kennedy et al., "An investigation of the thermal inactivation of *Staphylococcus aurues* and the potential for increased thermotolerance as a result of chilled storage," Journal of Applied Microbiology, 2005, 7 pages.

Krishnamurthy et al., "Inactivation of *Staphylococcus aureus* by Pulsed UV-Light Sterilization," Abstract, Journal of Food Protection, 2004, 1 page.

Krishnamurthy et al., "Inactivation of *Staphylococcus aureus* in Milk and Milk Foam by Pulsed UV-Light Treatment and Su+R170rface Response Modeling," Abstract, American Society of Agriculutural and Biological Engineers, 2013, 1 page.

Krishnamurthy et al., "Inactivation of *Staphylococcus aureus* in Milk Using Flow-Through Pulsed UV-Light Treatment System," Journal of Food Science, 2007, 7 pages, vol. 72, No. 7.

Krishnamurthy et al., "Microscopic and Spectroscopic Evaluation of Inactivation of *Staphylococcus aureus* by Pulsed UV Light and Infrared Heating," Food Bioprocess Technology, 2010, 12 pages.

Ozer et al., "Inactivation of *Escherichia coli* O157:H7 and Listeria monocytogenes inoculated on raw salmon fillets by pulsed UV-light treatment," International Journal of Food Science and Technology, 2006, 7 pages.

Sharma et al., "Inactivation of *Escherichia coli* O157:H7 on Inoculated Alfalfa Seed with Pulsed Ultraviolet Light and Response Surface Modeling," Food Microbiology and Safety, 2003, 6 pages.

Zang et al., "Nonthermal Processing Technologies for Food," Chapters 18 and 19, IFT Press, 2011, 21 pages.

Mayekar, K., U.S. Appl. No. 14/012,682, Non-Final Rejection, dated Sep. 24, 2014, 20 pages.

Mayekar, K., U.S. Appl. No. 14/012,682, Notice of Allowance, dated Jan. 22, 2015, 16 pages.

Mayekar, K., U.S. Appl. No. 14/629,508, Non-Final Rejection, dated Jun. 13, 2017, 74 pages.

Martin, E., U.S. Appl. No. 14/012,667, Notice of Allowance, dated Jun. 16, 2017, 25 pages.

Martin, E., U.S. Appl. No. 14/012,667, Final Rejection2, dated Nov. 30, 2016, 25 pages.

Martin, E., U.S. Appl. No. 14/012,667, Non-Final Rejection, dated Dec. 3, 2015, 73 pages.

Martin, E., U.S. Appl. No. 14/012,667, Final Rejection 1, dated Apr. 1, 2016, 15 pages.

Martin, E., U.S. Appl. No. 14/012,667, Non-Final Rejection2, dated Jun. 28, 2016, 20 pages.

Martin, E., U.S. Appl. No. 14/541,245, Notice of Allowance, dated Apr. 3, 2017, 18 pages.

Martin, E., U.S. Appl. No. 14/541,245, Final Rejection 1, dated Nov. 28, 2016, 23 pages.

Martin, E., U.S. Appl. No. 14/541,245, Non-Final Rejection 1, dated Jun. 17, 2016, 60 pages.

Mendoza-Wilkenfe, E., U.S. Appl. No. 14/012,652, Notice of Allowance, dated Mar. 10, 2017, 37 pages.

Mendoza-Wilkenfe, E., U.S. Appl. No. 14/012,652, Final Rejection, dated Nov. 17, 2016, 22 pages.

Mendoza-Wilkenfe, E., U.S. Appl. No. 14/012,652, Non-Final Rejection, dated Jun. 1, 2016, 74 pages.

Stoffa, W., U.S. Appl. No. 14/012,644, Non-Final Rejection, dated Mar. 10, 2014, 30 pages.

Stoffa, W., U.S. Appl. No. 14/012,644, Final Rejection, dated Jul. 3, 2014, 18 pages.

Stoffa, W., U.S. Appl. No. 14/012,644, Non-Final Rejection, dated Oct. 21, 2014, 19 pages.

Stoffa, W., U.S. Appl. No. 14/012,644, Notice of Allowance, dated Apr. 1, 2015, 15 pages.

Stoffa, W., U.S. Appl. No. 14/012,644, Notice of Allowance, dated Jul. 9, 2015, 32 pages.

Stoffa, W., U.S. Appl. No. 14/937,090, Notice of Allowance, dated Mar. 2, 2017, 18 pages.

(56) References Cited

OTHER PUBLICATIONS

Stoffa, W., U.S. Appl. No. 14/937,090, Final Rejection, dated Oct. 27, 2016, 45 pages.
Stoffa, W., U.S. Appl. No. 14/937,090, Non-Final Rejection, dated Jun. 1, 2016, 45 pages.
Stoffa, W., U.S. Appl. No. 15/388,506, Non-Final Rejection, dated Apr. 12, 2017, 51 pages.
Cox, A., U.S. Appl. No. 14/012,637, Final Rejection, dated Feb. 2, 2017, 33 pages.
Cox, A., U.S. Appl. No. 14/012,637, Final Rejection1 (updated to Non-Final Rejection dated Nov. 18, 2016), dated Aug. 25, 2016, 27 pages.
Cox, A., U.S. Appl. No. 14/012,637, Non-Final Rejection, dated Feb. 19, 2016, 49 pages.
Cox, A., U.S. Appl. No. 14/012,637, Non-Final Rejection, dated Jun. 29, 2017, 35 pages.
Krishnamurthy et al., "Food Processing Operations and Modeling: Design and Analysis," UV Pasteurization of Food Materials, Chapter 11, 2009, 22 pages.
Stoffa, W., U.S. Appl. No. 15/388,506, Notice of Allowance, dated Sep. 6, 2017, 35 pages.
Mayekar, K., U.S. Appl. No. 14/629,508, Notice of Allowance, dated Nov. 16, 2017, 22 pages.
Li, X., Application No. 201380053801.8, Rejection Decision—with English translation, dated Nov. 6, 2017, 14 pages.
Cheng, X., Application No. 201380053723.1, Notice of Allowance, dated Mar. 3, 2017, 2 pages (There is no English translation available.).
Cheng, X., Application No. 201380053723.1, Office Action1 (with English translation), dated Jun. 6, 2016, 11 pages.
Zhou, Z., Application No. 201380056459.7, Office Action1 (with English translation), dated Jun. 14, 2017, 13 pages (received Jun. 30, 2017).
Zhou, Z., Application No. 201380053729.9, Office Action1 (with English translation), dated Mar. 14, 2017, 21 pages.
Li, X., Application No. 201380053801.8, Office Action2 (with English translation), dated Apr. 21, 2017, 16 pages (received May 5, 2017).
Li, X., Application No. 201380053801.8, Office Action1 (with English translation), dated Jul. 22, 2016, 7 pages.
Kim, International Application No. PCT/US2013/057077, Search Report and Written Opinion, dated Nov. 8, 2013, 12 pages.
Yang, International Application No. PCT/US2013/056997, Search Report and Written Opinion, dated Nov. 28, 2013, 12 pages.
Yang, International Application No. PCT/US2013/056986, Search Report and Written Opinion, dated Nov. 29, 2013, 12 pages.
Yang, International Application No. PCT/US2013/056983, Search Report and Written Opinion, dated Dec. 19, 2013, 12 pages.
Mayekar, K., U.S. Appl. No. 15/388,394, Office Action1, dated Mar. 30, 2018, 81 pages.
Mendoza-Wilkenfe, E., U.S. Appl. No. 14/012,652, Office Action1, dated Apr. 9, 2018, 68 pages.
Mayekar, K., U.S. Appl. No. 15/700,533, Office Action1, dated May 22, 2018, 68 pages.
Zhou, Z., Application No. 201380056459.7, Notice of Allowance (There is no English translation available.), dated Mar. 13, 2018, received on May 16, 2018, 2 pages.
Martin, E., U.S. Appl. No. 15/982,611, Non-Final Rejection, dated Aug. 1, 2018, 31 pages.
Zhou, Z., Application No. 201380053729.9, Rejection Devision (with English translation), Jul. 25, 2018, received Aug. 22, 2018, 13 pages.
Stoffa, W., U.S. Appl. No. 15/856,978, Office Action, dated Sep. 7, 2018, 30 pages.
Mayekar, K., U.S. Appl. No. 15/700,533, Notice of Allowance, dated Sep. 21, 2018, 8 pages.
Mendoza-Wilkenfe, E., U.S. Appl. No. 14/012,652, Final Office Actionl, dated Sep. 4, 2018, 13 pages.
Mayekar, K., U.S. Appl. No. 15/388,394, Final Office Action, dated Nov. 9, 2018, 7 pages.

\* cited by examiner

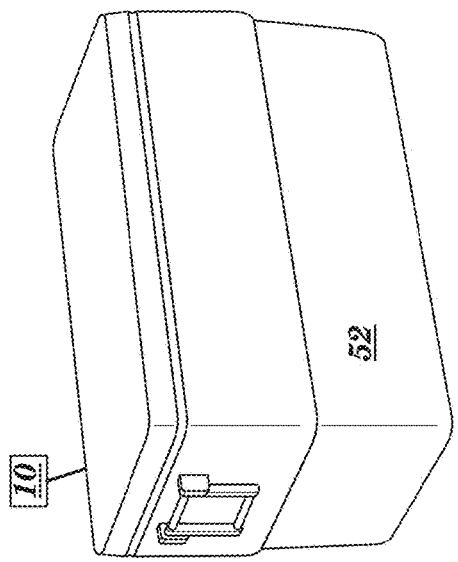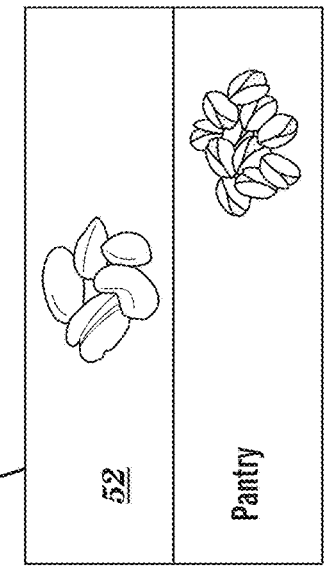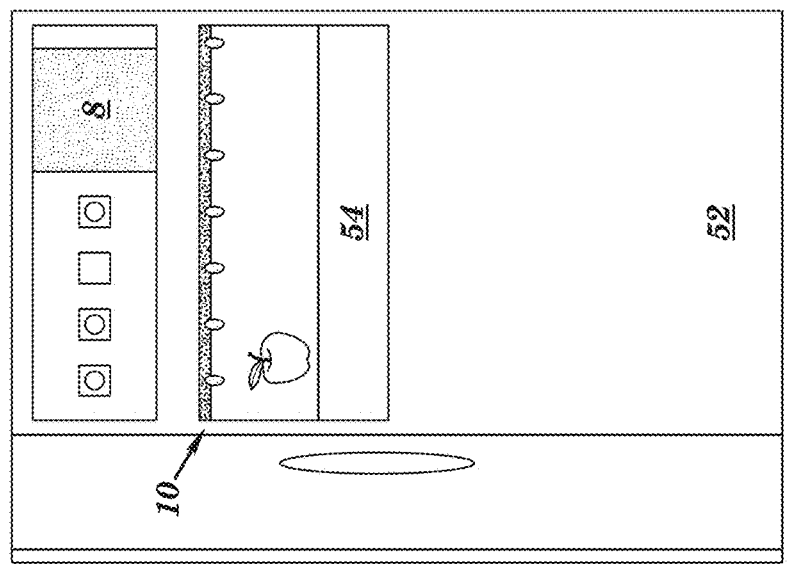
FIG. 4B
FIG. 4C
FIG. 4A

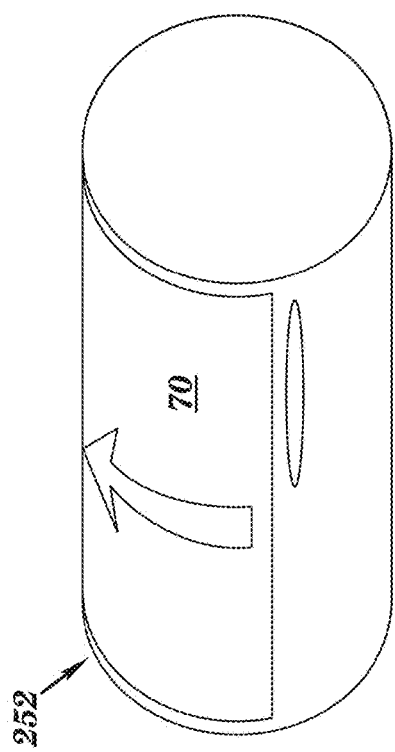
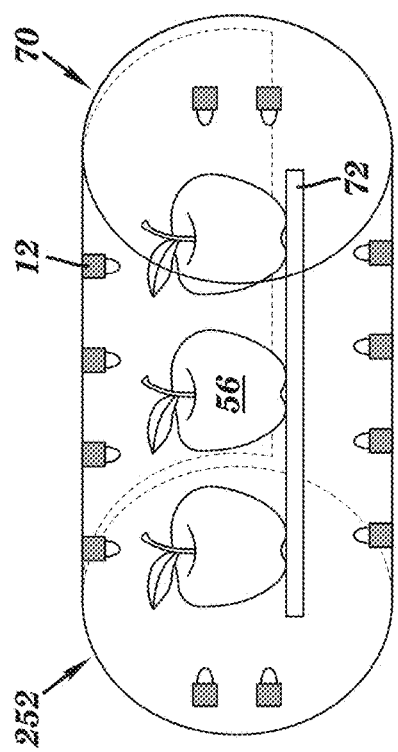
FIG. 6A
FIG. 6B

STORAGE DEVICE INCLUDING TARGET UV ILLUMINATION RANGES

REFERENCE TO RELATED APPLICATIONS

The current application is a continuation application of U.S. patent application Ser. No. 14/541,245, filed on 14 Nov. 2014, which claims the benefit of U.S. Provisional Application No. 61/904,119, which was filed on 14 Nov. 2013, and U.S. Provisional Application No. 61/989,891, which was filed on 7 May 2014, and which is a continuation-in-part application of U.S. application Ser. No. 14/012,667, filed on 28 Aug. 2013, which claims the benefit of U.S. Provisional Application No. 61/694,232, which was filed on 28 Aug. 2012, and U.S. Provisional Application No. 61/694,229, which was filed on 28 Aug. 2012, all of which are hereby incorporated by reference.

TECHNICAL FIELD

The disclosure relates generally to ultraviolet radiation, and more particularly, to a solution for preserving, disinfecting, and/or the like, stored items within an area, such as food items located in a storage area of a refrigerated unit, using ultraviolet radiation at target wavelength ranges.

BACKGROUND ART

Ultraviolet (UV) radiation has been utilized in various applications including biomedical and analytical instrumentation, defense, biotechnology, medicine, air, water, and surface sterilization and decontamination, bio-agent detection and identification, radiation hard UV sources, and UV curing. In many instances, UV radiation is used to manipulate the surfaces of objects, such as in sterilization, but various advanced manipulation of objects and their surfaces are feasible with UV radiation. For example, UV curing technology applies ultraviolet light to resins such as coatings, adhesives, marking ink and photo-resists, etc., to cause photopolymerization. UV technology has also been applied in medical applications, such as skin cancer treatment, sterilization, and increasing vitamin D3 (cholecalciferol). Vitamin D3, for example, is produced through the action of ultraviolet irradiation on its precursor 7-dehydrocholesterol. Vitamin D3 can be made by exposure of the human skin to UV, or by exposing milk directly to UV. Another use for UV radiation is found in food preservation and food modification applications.

Reliable, hygienic storage of sanitary and biological items, such as food, is a major problem. For example, the problem is present throughout the food industry, e.g., manufacturers, retailers, restaurants, and in every household, and is especially significant for food service establishments, in which related issues of food quality control also are significant. In addition to food storage and quality control in fixed locations (e.g., a refrigerator) where access to electricity is readily available, proper food storage and quality control also is important in situations for which access to unlimited electricity and/or a stationary storage device, such as a refrigerator, is not available, such as picnics, camping, mobile food kiosks, hospitality or battlefield meal locations, search and rescue, etc. In addition to food, other stored items also require hygienic storage. For example, medical and chemical equipment, construction wood, etc., also require storage in a biologically safe environment. Since ambient temperature significantly affects bacterial activity, effective control of the ambient temperature is an important tool in ensuring reliable, hygienic storage of various items.

Fresh food products can be processed using ultraviolet light as a germicidal medium to reduce the food-born microbial load. Water has been treated with ultraviolet light to provide safe drinking water for quite some time. Fruit and vegetable products capable of being pumped through a system generally are very suitable for processing by ultraviolet light to reduce the microbial load. Today, most of these products are pasteurized to obtain microbiologically safe and nutritious products. However, pasteurization can change the taste and flavor of such products because of the temperature and processing time. Juices from different sources can be treated by exposure to ultraviolet light at different doses. On the other hand, variables such as exposure time, type of fruit product, juice color and juice composition, among other variables, need to be studied to obtain fruit products with reduced microbial load, increased shelf life and adequate sensory and nutritional characteristics. Reduction of microbial load through ultraviolet light application as a disinfection medium for food products other than liquids also is being studied. Moreover, ultraviolet technology could be a source for pasteurization of liquids, or disinfection of solid foods as an alternative technology, instead of thermal treatment or application of antimicrobial compounds.

In general, ultraviolet (UV) light is classified into three wavelength ranges: UV-C, from about 200 nanometers (nm) to about 280 nm; UV-B, from about 280 nm to about 315 nm; and UV-A, from about 315 nm to about 400 nm. Generally, ultraviolet light, and in particular, UV-C light is "germicidal," i.e., it deactivates the DNA of bacteria, viruses and other pathogens and thus destroys their ability to multiply and cause disease. This effectively results in sterilization of the microorganisms. Specifically, UV-C light causes damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. UV light with a wavelength of approximately between about 250 to about 280 nm provides the highest germicidal effectiveness. While susceptibility to UV light varies, exposure to UV energy for about 20 to about 34 milliwatt-seconds/cm$^2$ is adequate to deactivate approximately 99 percent of the pathogens.

Various approaches have sought to use ultraviolet light to disinfect a compartment, such as compartments found in refrigerators. For example, one approach proposes a plurality of small, low current UV lights which utilize the standard circuitry of the refrigerator to power the UV light source. Another approach uses a UV lamp installed in a top portion of the refrigerator and reflective lining throughout the interior to reflect the UV radiation throughout the compartment. Another approach provides a UV system with a single UV source attached to an internal sidewall of a refrigerator to radiate light to the entire compartment, or in the alternative, provide UV exposure to a limited compartment. Still another approach proposes an air cleaner for an internal compartment of a refrigerator, which utilizes a UV filter to reduce pathogens in the re-circulated air. Still another approach provides a refrigerator with UV light irradiation components to eradicate low-level light from the storage containers contained therein to promote freshness of foodstuffs.

SUMMARY OF THE INVENTION

While refrigerators have been widely used to maintain freshness of foods stored therein, and several approaches for using UV light devices in connection with refrigerators have been proposed, the inventors recognize that these approaches fail to adequately address the issue of food storage life prolongation, disinfection, and ethylene decomposition through UV radiation of specific wavelength and/or intensities in conjunction with UV sources comprising ultraviolet light emitting diodes.

The inventors provide a solution for preserving and/or disinfecting stored items within an area, such as a storage area of a refrigerated unit, using ultraviolet radiation at target wavelength ranges and/or target intensity ranges. For example, an embodiment of the solution is configured to appropriately apply a target intensity and wavelength for ultraviolet radiation to preserve and/or disinfect food items without affecting the quality of the food items. Similarly, this solution may apply to items that are within other storage environments, such as pantries, grocery bags, boxes, biological object storage containers, and/or the like.

Aspects of the invention provide a solution in which ultraviolet radiation is directed within an area at target wavelength ranges and/or target intensity ranges. The target wavelength ranges and/or target intensity ranges of the ultraviolet radiation sources can be configured to correspond to at least one of a plurality of selectable operating configurations including a storage life preservation operating configuration, a disinfection operating configuration, and an ethylene decomposition operating configuration.

A first aspect of the invention provides a system comprising: at least one ultraviolet radiation source configured to generate ultraviolet radiation directed within a storage area; and a monitoring and control system for managing the storage area by performing a method comprising: monitoring a set of current conditions of at least one of: the storage area or a set of items located in the storage area; and controlling ultraviolet radiation generated by the at least one ultraviolet radiation source using at least one of a plurality of selectable operating configurations and the set of current conditions, the selectable operating configurations including: a storage life preservation operating configuration, a disinfection operating configuration, and an ethylene decomposition operating configuration, wherein each selectable operating configuration mode has a corresponding target intensity range and a target wavelength range for the ultraviolet radiation.

A second aspect of the invention provides a food storage device comprising: a storage area configured to store at least one perishable food item; at least one ultraviolet radiation source configured to generate ultraviolet radiation directed within the storage area; and a monitoring and control system for managing the storage area by performing a method comprising: monitoring a set of current conditions of at least one of: the storage area or a set of items located in the storage area; and controlling ultraviolet radiation generated by the at least one ultraviolet radiation source using at least one of a plurality of selectable operating configurations and the set of current conditions, the selectable operating configurations including: a storage life preservation operating configuration, a disinfection operating configuration, and an ethylene decomposition operating configuration, wherein each selectable operating configuration mode has a corresponding target intensity range and a target wavelength range for the ultraviolet radiation.

A third aspect of the invention provides a refrigeration device comprising: a storage area configured to store at least one refrigerated item; a component configured to control at least one environmental condition of the storage area, wherein the at least one environmental condition includes at least one of: a temperature, a humidity, a gas convection, or a fluid convection; at least one ultraviolet radiation source configured to generate ultraviolet radiation directed within the storage area; and a monitoring and control system for managing the storage area by performing a method comprising: monitoring a set of current conditions of at least one of: the storage area or a set of items located in the storage area; and controlling ultraviolet radiation generated by the at least one ultraviolet radiation source using at least one of a plurality of selectable operating configurations and the set of current conditions, the selectable operating configurations including: a storage life preservation operating configuration, a disinfection operating configuration, and an ethylene decomposition operating configuration, wherein each selectable operating configuration mode has a corresponding target intensity range and a target wavelength range for the ultraviolet radiation.

A fourth aspect of the invention provides a system comprising: a set of ultraviolet radiation sources configured to generate ultraviolet radiation directed at a set of items within a storage area; and a monitoring and control system for managing the ultraviolet radiation by performing a method comprising: monitoring a set of current conditions of at least one of: the storage area or the set of items located in the storage area; and controlling the ultraviolet radiation generated by the set of ultraviolet radiation sources using the set of current conditions and a target effect for the set of items by adjusting at least one of: an intensity, a wavelength, a temporal distribution, or a spatial distribution of the ultraviolet radiation.

A fifth aspect of the invention provides a device comprising: a set of ultraviolet radiation sources configured to generate ultraviolet radiation directed at a set of items within a storage area; and a monitoring and control system for managing the ultraviolet radiation by performing a method comprising: monitoring a set of current conditions of at least one of: the storage area or the set of items located in the storage area; and controlling the ultraviolet radiation generated by the set of ultraviolet radiation sources using the set of current conditions and a target effect for the set of items by adjusting at least one of: an intensity, a wavelength, a temporal distribution, or a spatial distribution of the ultraviolet radiation.

A sixth aspect of the invention provides a refrigeration device comprising: a storage area configured to store at least one refrigerated item; a component configured to control at least one environmental condition of the storage area, wherein the at least one environmental condition includes at least one of: a temperature, a humidity, a gas convection, or a fluid convection; at least one ultraviolet radiation source configured to generate ultraviolet radiation directed within the storage area; and a monitoring and control system for managing the storage area by performing a method comprising: monitoring a set of current conditions of at least one of: the storage area or the set of items located in the storage area; and controlling the ultraviolet radiation generated by the set of ultraviolet radiation sources using the set of current conditions and a target effect for the set of items by adjusting at least one of: an intensity, a wavelength, a temporal distribution, or a spatial distribution of the ultraviolet radiation.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 4A-4C show illustrative storage devices for use with an ultraviolet radiation system according to embodiments.

FIGS. 6A and 6B show perspective views of illustrative storage devices according to embodiments.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution in which ultraviolet radiation is directed within an area and/or towards a target object within an area at target wavelengths, target intensities, target spatial distributions, and/or target temporal distributions. The target wavelengths, target intensities, target spatial distributions, and/or target temporal distributions of the ultraviolet radiation sources can correspond to at least one of a plurality of selectable operating configurations including a storage life preservation operating configuration, a disinfection operating configuration, and an ethylene decomposition operating configuration. In another embodiment, the selectable operating configurations can be defined based on a target effect on an item, such as suppressing microorganism growth, maintaining and/or improving nutritional value of food, maintaining and/or improving visual appearance of the item, changing a chemical composition of the material at the surface of the item, and/or the like. In either case, one or more properties of the UV radiation can be controlled based on the operating configuration and/or to induce a target effect on an item.

As used herein, unless otherwise noted, the term "set" means one or more (i.e., at least one) and the phrase "any solution" means any now known or later developed solution. Furthermore, as used herein, ultraviolet radiation/light means electromagnetic radiation having a wavelength ranging from approximately 10 to approximately 400 nanometers, ultraviolet-C (UV-C) means electromagnetic radiation having a wavelength ranging from approximately 100 to approximately 280 nanometers, ultraviolet-B (UV-B) means electromagnetic radiation having a wavelength ranging from approximately 280 to approximately 315 nanometers, and ultraviolet-A (UV-A) means electromagnetic radiation having a wavelength ranging from approximately 315 to approximately 400 nanometers. As also used herein, a material/structure is considered to be "reflective" to ultraviolet light of a particular wavelength when the material/structure has an ultraviolet reflection coefficient of at least thirty percent for the ultraviolet light of the particular wavelength. In a more particular embodiment, a highly ultraviolet reflective material/structure has an ultraviolet reflection coefficient of at least eighty percent. Furthermore, a material/structure is considered to be "transparent" to ultraviolet light of a particular wavelength when the material/structure allows a significant amount of the ultraviolet radiation to pass there through. In an embodiment, the ultraviolet transparent structure is formed of a material and has a thickness, which allows at least ten percent of the ultraviolet radiation to pass there through.

Figure 1:
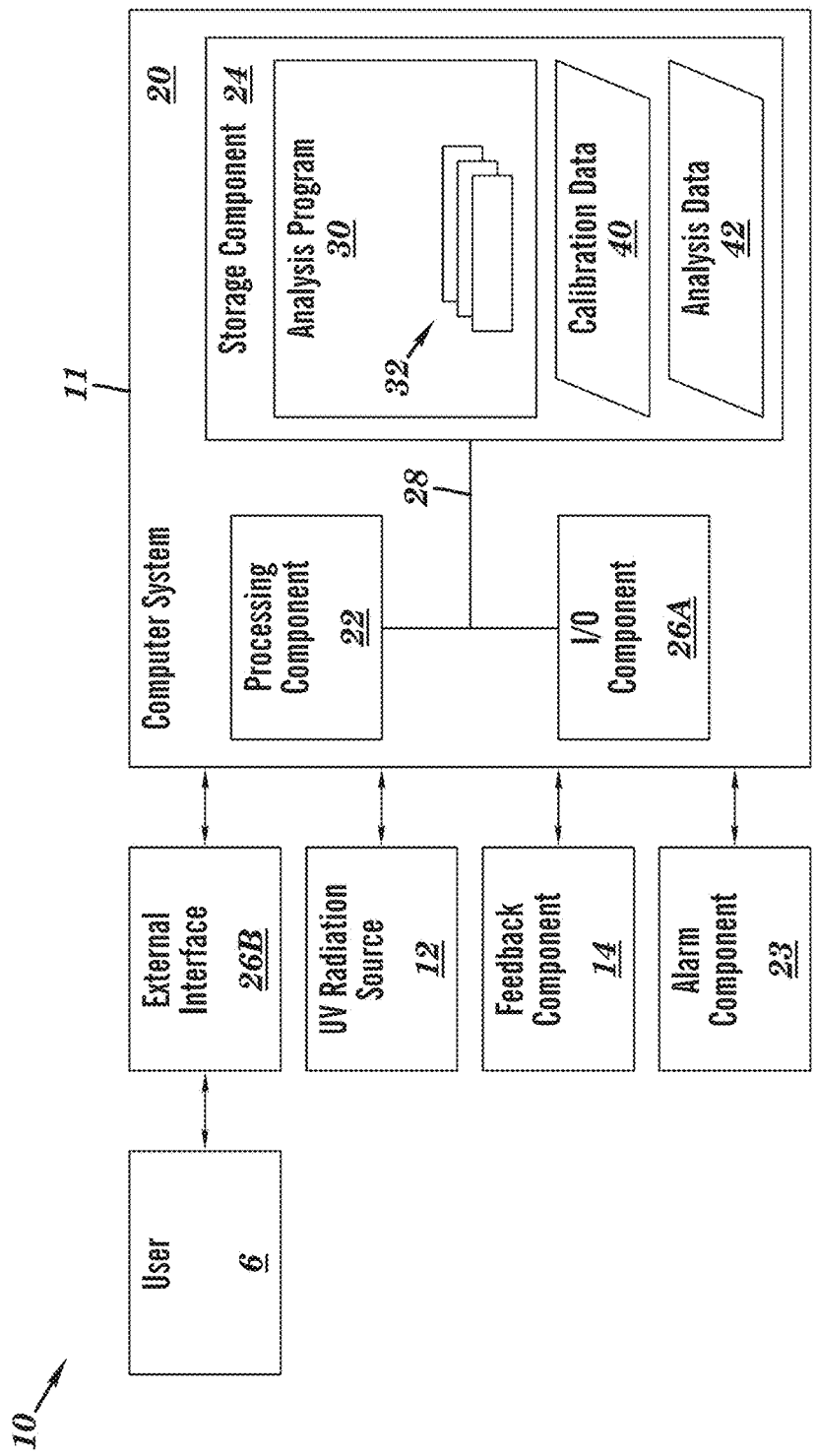
FIG. 1 shows an illustrative ultraviolet radiation system according to an embodiment.

Turning to the drawings, FIG. 1 shows an illustrative ultraviolet radiation system 10 according to an embodiment. In this case, the system 10 includes a monitoring and/or control system 11, which is implemented as a computer system 20 including an analysis program 30, which makes the computer system 20 operable to manage an ultraviolet (UV) radiation source 12 by performing a process described herein. In particular, the analysis program 30 can enable the computer system 20 to operate the UV radiation source 12 to generate and direct ultraviolet radiation within an area and process data corresponding to one or more current conditions of the area and/or an item located in the area, which is acquired by a feedback component 14. While a single UV radiation source 12 is shown, it is understood that the area can include any number of UV radiation sources 12, the operation of which the computer system 20 can separately manage using a process described herein.

In an embodiment, during an initial period of operation (e.g., after recent access to the area, addition/removal/reconfiguration of item(s) placed within the area, and/or the like), the computer system 20 can acquire data from the feedback component 14 regarding one or more attributes of the item(s) in the area and/or conditions of the area and generate analysis data 42 for further processing. The analysis data 42 can include information on the color(s), a distribution of the colors, an appearance, and/or the like, of item(s) in the area, the presence of microorganisms on the item(s) or within the area, a change of the material of an item, a measured amount of reflected radiation (e.g., UV, visible, ionized, infrared, and/or the like) from an item, a transparency of an area surrounding an item, a temperature over a surface of an item, and/or the like. Analysis data 42 also can include information on a total UV radiation dose. Furthermore, the analysis data 42 can include information on the presence of a chemical (e.g., ethylene gas) within the area. The computer system 20 can use the analysis data 42 to generate calibration data 40 for controlling one or more aspects of the ultraviolet radiation generated by the ultraviolet radiation source(s) 12 using one of a plurality of selectable operating configurations as discussed herein. Furthermore, one or more aspects of the operation of the ultraviolet radiation source 12 can be controlled by a user 6 via an external interface component 26B.

The computer system 20 is shown including a processing component 22 (e.g., one or more processors), a storage component 24 (e.g., a storage hierarchy), an input/output (I/O) component 26A (e.g., one or more I/O interfaces and/or devices), and a communications pathway 28. In general, the processing component 22 executes program code, such as the analysis program 30, which is at least partially fixed in the storage component 24. While executing program code, the processing component 22 can process data, which can result in reading and/or writing transformed data from/to the storage component 24 and/or the I/O component 26A for further processing. The pathway 28 provides a communications link between each of the components in the computer system 20. The I/O component 26A and/or the external interface component 26B can comprise one or more human I/O devices, which enable a human user 6 to interact with the computer system 20 and/or one or more communications devices to enable a system user 6 to communicate with the computer system 20 using any type of communications link. To this extent, during execution by the computer system 20, the analysis program 30 can manage a set of interfaces (e.g., graphical user interface(s), application program interface, and/or the like) that enable human and/or system users 6 to interact with the analysis program 30. Furthermore, the analysis program 30 can manage (e.g., store, retrieve, create, manipulate, organize, present, etc.) the data, such as calibration data 40 and analysis data 42, using any solution.

In any event, the computer system 20 can comprise one or more general purpose computing articles of manufacture (e.g., computing devices) capable of executing program code, such as the analysis program 30, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 30 can be embodied as any combination of system software and/or application software.

Furthermore, the analysis program 30 can be implemented using a set of modules 32. In this case, a module 32 can enable the computer system 20 to perform a set of tasks used by the analysis program 30, and can be separately developed and/or implemented apart from other portions of the analysis program 30. When the computer system 20 comprises multiple computing devices, each computing device can have only a portion of the analysis program 30 fixed thereon (e.g., one or more modules 32). However, it is understood that the computer system 20 and the analysis program 30 are only representative of various possible equivalent monitoring and/or control systems 11 that may perform a process described herein. To this extent, in other embodiments, the functionality provided by the computer system 20 and the analysis program 30 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 11 can be implemented without any computing device, e.g., using a closed loop circuit implementing a feedback control loop in which the outputs of one or more sensing devices are used as inputs to control the operation of one or more other devices (e.g., LEDs). Illustrative aspects of the invention are further described in conjunction with the computer system 20. However, it is understood that the functionality described in conjunction therewith can be implemented by any type of monitoring and/or control system 11.

Regardless, when the computer system 20 includes multiple computing devices, the computing devices can communicate over any type of communications link. Furthermore, while performing a process described herein, the computer system 20 can communicate with one or more other computer systems, such as the user 6, using any type of communications link. In either case, the communications link can comprise any combination of various types of wired and/or wireless links; comprise any combination of one or more types of networks; and/or utilize any combination of various types of transmission techniques and protocols. This communications link, which can include a wireless or cable based transmission, can be utilized to transmit information about the state of one or more items and/or zones within the storage area 54.

The system 10 can be implemented within an existing storage device (e.g., a refrigerator) using any solution. For example, one or more ultraviolet radiation sources 12 and one or more devices included in a feedback component 14 can be fixed within various locations in the storage device (e.g., on walls, shelves, etc.) and configured for operation by the computer system 20. The locations of devices in the ultraviolet radiation source(s) 12 and/or the feedback component 14 can be selected to provide comprehensive coverage of the storage area of the storage device and the items located within the storage area. In an embodiment, the computer system 20 can be located outside of the storage area of the storage device.

The ultraviolet radiation source 12 can comprise any combination of one or more ultraviolet radiation emitters. For example, the UV source 12 can include a high intensity ultraviolet lamp (e.g., a high intensity mercury lamp), an ultraviolet light emitting diode (LED), an ultraviolet laser diode, and/or the like. In an embodiment, the UV source 12 includes a set of light emitting diodes manufactured with one or more layers of materials selected from the group-III nitride material system (e.g., $Al_xIn_yGa_{1-X-Y}N$, where $0 \leq x$, $y \leq 1$, and $x+y \leq 1$ and/or alloys thereof). In an embodiment including a set of ultraviolet laser diodes, the system can be used, for example, for UV lithography. Additionally, the UV source 12 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, within the storage area. Illustrative wave guiding structures include, but are not limited to, a plurality of ultraviolet fibers, each of which terminates at an opening, a diffuser, and/or the like. The computer system 12 can independently control each UV source 12.

The system 10 also can include an alarm component 23, which can be operated by the computer system 20 to indicate when ultraviolet radiation is being directed within the storage area. The alarm component 23 can include one or more devices for generating a visual signal, an auditory signal, and/or the like. For example, in the example shown in FIG. 4A, where the storage device 52 includes a refrigeration device, a panel 8 can display a flashing light, text, an image, and/or the like, to indicate that ultraviolet radiation is currently being directed into a corresponding storage area 54. Furthermore, the alarm component 23 can generate a noise, such as a bell, a beep, and/or the like, to indicate that ultraviolet radiation is currently being directed to the storage area 54.

Figure 2:
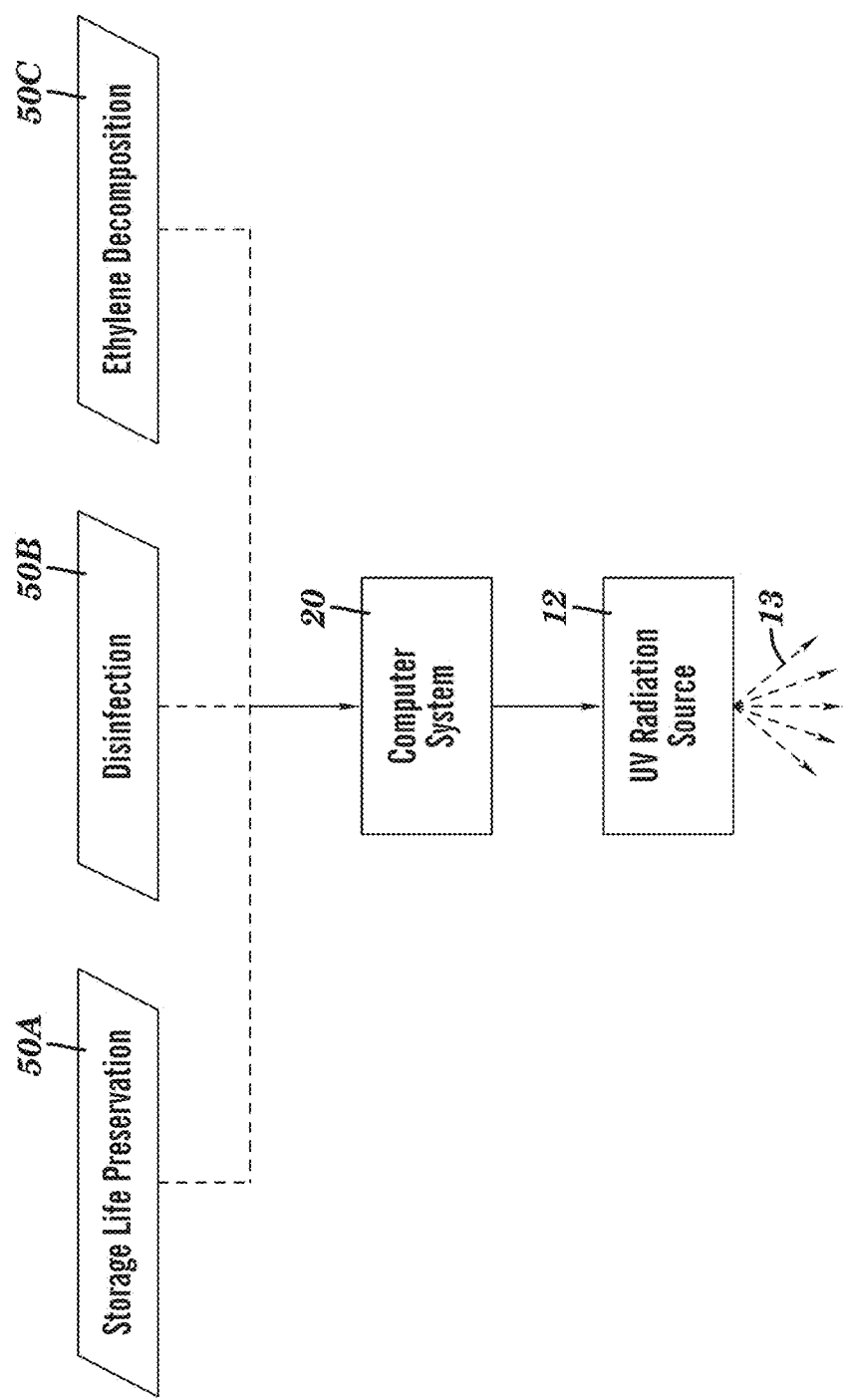
FIG. 2 shows a block diagram illustrating use of operating configurations for operating an ultraviolet radiation source according to an embodiment.

FIG. 2 shows a block diagram illustrating use of operating configurations for operating an ultraviolet radiation source 12 according to an embodiment. As illustrated, the computer system 20 can use data corresponding to a selected operating configuration 50A-50C to adjust one or more aspects of the ultraviolet radiation 13 generated by the ultraviolet radiation source(s) 12. In an embodiment, the operating configurations 50A-50C can include a storage life preservation operating configuration 50A, a disinfection operating configuration 50B, and an ethylene decomposition operating configuration 50C. In an embodiment, the storage life preservation operating configuration 50A is configured to increase a storage lifespan of items stored within the area, while the disinfection operating configuration 50B is configured to eliminate and/or decrease an amount of microorganisms present within the area or on item(s) located within the area. The ethylene decomposition operating configuration 50C can be configured to remove ethylene from the atmosphere of the storage area, which would otherwise decrease the storage lifespan of items located within the area. One or more of these operating configurations can be configured to improve and/or maintain the visual appearance and/or nutritional value of the items within the storage area. For example, increasing the storage lifespan can include suppressing microorganism growth, maintaining and/or improving nutritional value, maintaining and/or improving visual appearance, and/or the like. Also, the operating configurations can be configured to prevent the build-up of mold within the storage area and/or on the items within the storage area.

The computer system 20 can be configured to control and adjust a direction, an intensity, a pattern, a spectral power (e.g., wavelength), a temporal distribution, a spatial distribution, and/or the like, of UV radiation emitted by the UV sources 12. The control and adjustment of the UV sources 12 and the resulting UV radiation can correspond to a particular operating configuration 50A-50C and/or be in response to data from the feedback component 14. The computer system 20 can control and adjust each property of the UV source 12 independently. For example, the computer system 20 can adjust the intensity, the time duration, and/or time scheduling (e.g., pattern or temporal distribution) of the UV source 12 for a given wavelength and/or a given spatial distribution. Each operating configuration 50A-50C can designate a unique combination of: a target ultraviolet wavelength, a target intensity level, a target pattern, a target temporal distribution for the ultraviolet radiation (e.g., time scheduling, including duration (e.g., exposure/illumination time), duty cycle, time between exposures/illuminations, and/or the like), a target spectral power, a target spatial distribution, and/or the like, in order to meet a unique set of goals corresponding to each operating configuration 50A-50C.

For the storage life preservation operating configuration 50A, a target wavelength range can be approximately 285 nanometers to approximately 305 nanometers. The wavelength is specified in terms of its peak emission, and a characteristic half width of the emission can be approximately 1 nanometer to approximately 30 nanometers. The target intensity range for the storage life prolongation operating configuration 50A can be approximately 0.1 milliwatts/m$^2$ to approximately 1000 milliwatts/m$^2$. For the disinfection operating configuration 50B, a target wavelength range can be approximately 250 nanometers to approximately 285 nanometers. The wavelength is specified in terms of its peak emission, and a characteristic half width of the emission can be approximately 1 nanometer to approximately 35 nanometers. The target intensity range for the disinfection operating configuration 50B can be approximately 1 milliwatt/m$^2$ to approximately 10 watts/m$^2$. For the ethylene decomposition operating configuration 50C, the target wavelength range can be is approximately 230 nanometers to approximately 260 nanometers. The wavelength is specified in terms of its peak emission, and a characteristic half width of the mission can be approximately 1 nanometer to approximately 30 nanometers. The target intensity range for the ethylene decomposition operating configuration 50C can be approximately 1 milliwatt/m$^2$ to approximately 1000 watts/m$^2$.

Figure 3:
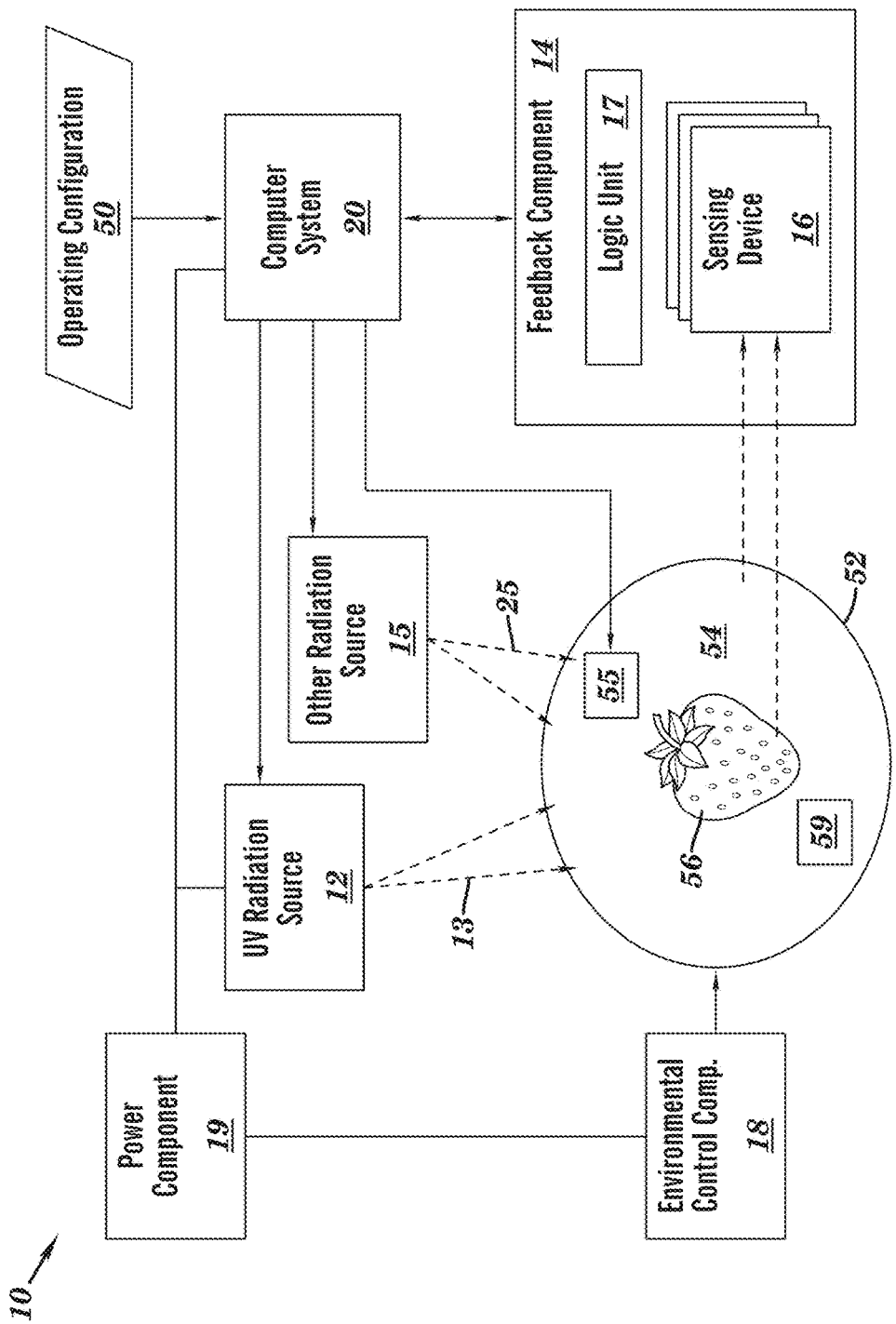
FIG. 3 shows an illustrative system including an ultraviolet radiation system according to an embodiment.

FIG. 3 shows an illustrative system including an ultraviolet radiation system 10 according to an embodiment. The computer system 20 is configured to control the UV source 12 to direct ultraviolet radiation 13 into a storage area 54 of a storage device 52, within which a set of items 56 are located. Although FIG. 3 shows item 56 as a food item, it is understood that this is only illustrative of various types of items 56, and that item 56 can include any type of item. The feedback component 14 is configured to acquire data used to monitor a set of current conditions of the storage area 54 and/or the items 56 over a period of time. As illustrated, the feedback component 14 can include a plurality of sensing devices 16, each of which can acquire data used by the computer system 20 to monitor the set of current conditions. A logic unit 17 can evaluate data acquired by one or more of the sensing devices 16 to quantitatively determine the target effect using any solution. The logic unit 17 can be implemented using any solution, e.g., as one or more computing devices and/or a closed loop circuit implementing a feedback control loop as described herein.

In an embodiment, the sensing devices 16 include at least one of a visual camera or a chemical sensor. The visual camera can acquire data (e.g., visual, electronic, and/or the like) used to monitor the storage area 54 and/or one or more of the items 56 located therein, while the chemical sensor can acquire data (e.g., chemical, electronic, and/or the like) used to monitor the storage area 54 and/or one or more of the items 56 located therein. The set of current conditions of the storage area 54 and/or items 56 can include the color or visual appearance of the items 56, the presence of microorganisms within the storage area 54, the chemical composition of the item 56, the temperature of the surface of the item 56, and/or the like. In an embodiment, the visual camera comprises a fluorescent optical camera, such as a visible photo-detector. In this case, when the computer system 20 is operating the UV radiation source 12 in the storage life preservation operating configuration 50A (FIG. 2), the visual camera can be operated to detect the presence of microorganisms as they fluoresce in the ultraviolet light.

In another embodiment, another radiation source 15 can include one or more auxiliary light emitters (e.g., visible radiation, ionization radiation, infrared (IR), and/or the like) that emit radiation in the wavelength range of approximately 240 nanometers to approximately 900 nanometers. The auxiliary light emitters can be beneficial to the plants for various chemical processes that occur in the plants. Furthermore, the auxiliary light emitters can be used as a light needed for visual inspection of the items and the effect of the UV radiation on the items. In another embodiment, the auxiliary light emitters can also excite a fluorescence signal on the set of items that can indicate the presence of microorganisms. The visual inspection can include recording an image of the item 56 using the visual camera, which can be used by the computer system 20 for analysis. The sensing devices 16 can also include detectors of ultraviolet, visible, ionized and/or infrared (IR) radiation reflected off of or emitted by the item 56. Such detectors can include, for example, UV photo-detectors, such as, group III nitride solid state semiconductors, and/or the like.

In an embodiment, the chemical sensor is an infrared sensor, which is capable of detecting any combination of one or more gases, such as ethylene, ethylene oxide, and/or the like. However, it is understood that a visual camera and a chemical sensor are only illustrative of various types of sensors that can be implemented. For example, the sensing devices 16 can include one or more mechanical sensors (including piezoelectric sensors, various membranes, cantilevers, a micro-electromechanical sensor or MEMS, a nano-mechanical sensor, and/or the like), which can be configured to acquire any of various types of data regarding the storage area 54 and/or items 56 located therein. In the ethylene decomposition operating configuration 50C, the storage device 52 can include a high efficiency ethylene destruction chamber 55 that includes a high UV reflectivity, high UV intensity radiation chamber for chemical (e.g., ethylene) destruction. In this embodiment, the computer system 20 can operate the one or more devices in the chamber 55 to destroy ethylene, which may be present within the atmosphere of the storage area 54. The computer system 20 can separately monitor the ethylene levels and the level of microorganism activity.

The feedback component 14 also can include one or more additional devices. For example, the feedback component 14 is shown including a logic unit 17. In an embodiment, the logic unit 17 receives data from a set of sensing devices 16 and provides data corresponding to the set of conditions of the storage area 54 and/or items 56 located in the storage area 54 for processing by the computer system 20. In a more particular embodiment, the computer system 20 can provide information corresponding to the currently selected operating configuration 50 for use by the feedback component 14. For example, the logic unit 17 can adjust the operation of one or more of the sensing devices 16, operate a unique subset of the sensing devices 16, and/or the like, according to the currently selected operating configuration 50. In response to data received from the feedback component 14, the computer system 20 can automatically adjust and control one or more aspects of the ultraviolet radiation 13 generated by the ultraviolet radiation source 12 according to the currently selected operating configuration 50. In another embodiment, the computer system 20 can automatically adjust and control one or more aspects of the ultraviolet radiation 13 generated by the UV sources 12 according to the desired effect on the item 56, e.g., based on the data from the feedback component 14.

In the ethylene decomposition operating configuration 50C, the storage area 54 can include a catalyst 59 for reducing ethylene levels within the storage area 54, e.g., via a photocatalytic reaction. The catalyst 59 can include titanium dioxide, and/or the like. The catalyst 59 also can be configured to chemically inactivate or absorb the ethylene gas. In an embodiment, the computer system 20 can operate one or more devices of the environmental control component 18 in order to selectively introduce the catalyst 59 into the storage area 54. In another embodiment, the environmental control component 18 can automatically introduce the catalyst 59 into the storage area 54 according to a target level of the catalyst 59 and/or a preset schedule. The catalyst 59 also can be used for affecting the chemical reactions due to the UV radiation.

As described herein, in an embodiment, the system 10 can include another radiation source 15 (e.g., visible radiation, ionization radiation, infrared (IR), and/or the like) which can be controlled by the computer system 20 to generate light 25 directed within the storage area 54. For example, the computer system 20 can control the other radiation source 15 to generate light 25 (e.g., visible) with wavelengths configured to increase photosynthesis in one or more food items 56. Additionally, the computer system 20 can control the other radiation source 15 to generate light 25 (e.g., infrared) directed onto certain foods to locally increase the temperature of the items 56 (e.g., food). The increased temperature can result in an increase in the chemical reaction in that part of the item 56. The other radiation source 15 also can be configured to generate light 25 to excite fluorescence from microorganisms that may be present on items 56, so that a sensing device 16 of the feedback component 14 can detect the microorganisms. Furthermore, the other radiation source 15 can generate light 25 to facilitate a target (e.g., optimal) photocatalytic reaction for the catalyst 59.

In an embodiment, the computer system 20 can control the intensity, the wavelength, the temporal distribution, the spatial distribution, and/or the like, of UV radiation emitted by the UV radiation source 12 and/or other radiation emitted by the other radiation source 15 according to a set of current conditions monitored by the feedback component 14. For example, the computer system 20 can control one or more of these properties of the UV radiation source 12 and/or the other radiation source 15 to induce a particular desired effect on the target item(s) 56 located within the storage area 54.

Figure 9:
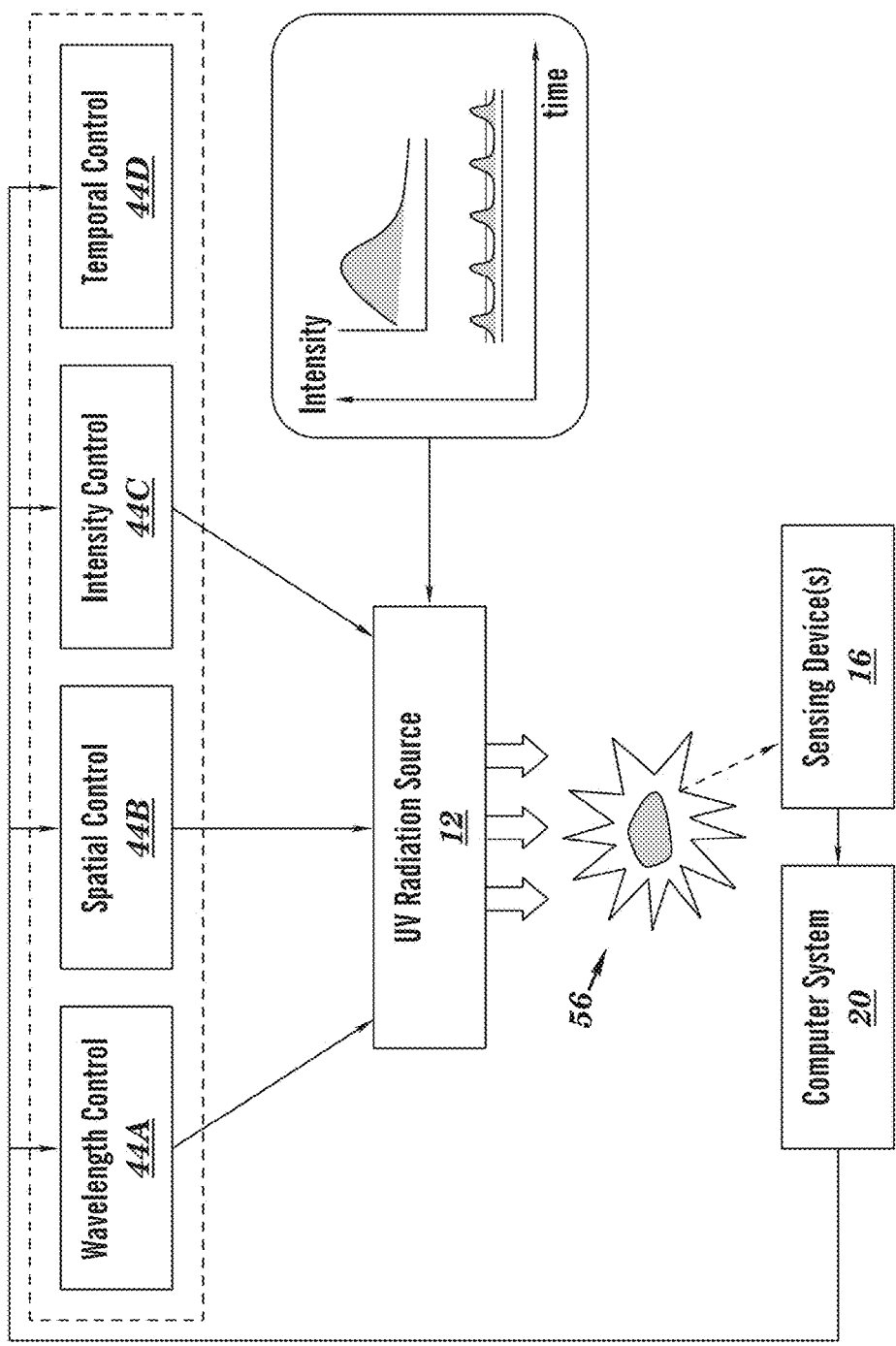
FIG. 9 shows a block diagram of illustrative control parameters for the UV source(s) according to an embodiment.

Turning now to FIG. 9, the computer system 20 is shown adjusting an illustrative set of control parameters 44A-44D of the UV radiation source 12 based on the feedback data from the sensing device(s) 16 according to an embodiment. For example, the feedback data can be processed by the computer system 20 to determine whether a desired effect has occurred, which the computer system 20 can use to adjust one or more of the set of control parameters 44A-44D. The desired effect can include: UV curing; a change in the chemical composition of the material of the item 56; disinfection and/or sterilization; treating a skin disease in a human and/or animal; increasing vitamin(s), antioxidants, and/or a life span of a plant; disinfection of tissue; destruction of DNA molecules; and/or the like. In each circumstance, one or more of the control parameters 44A-44D and resulting properties of the UV radiation generated by the UV radiation source 12 can be important to control for a particular desired effect. For example, a particular dose (e.g., intensity) of UV radiation may be required to induce a change in polyphenol compounds found in plants. In another example, the distribution of UV radiation may be more important with respect to disinfection and treatment of malignant spots on the skin. In this case, the spatial distribution can also be important to avoid exposing other portions of the skin to unwanted UV radiation. While the UV radiation source 12 is shown in FIG. 9, it is understood that the computer system 20 can similarly control radiation emitted by the other radiation source 15 (FIG. 3) using a similar set of control parameters 44A-44D.

Figure 8A:
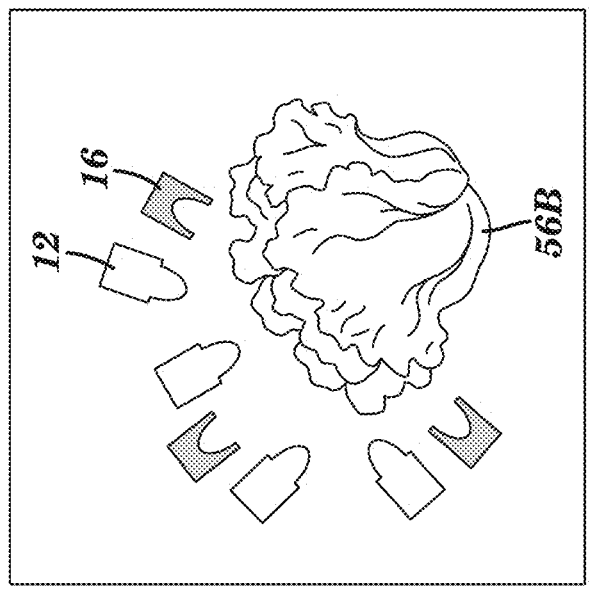
FIGS. 8A and 8B show schematics of an illustrative item and plant, respectively, receiving non-uniform UV radiation according to an embodiment.
Figure 8B:
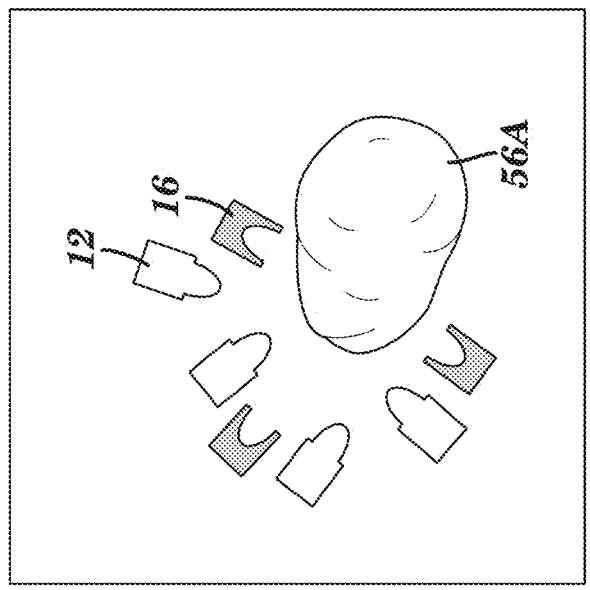

Turning now to FIGS. 8A and 8B, schematics are shown of an item 56A and a plant 56B, respectively, which are exposed to non-uniform UV radiation. For example, the UV radiation source 12 can include multiple UV sources configured to emit UV radiation directed towards one end of the item 56A and plant 56B. Similarly, as seen in the figures, the feedback component 14 (FIG. 3) can include sensing devices 16, which also can be adjusted spatially towards the direction of the UV radiation. In the embodiment including the plant 56B, it is understood that the UV radiation can be applied on a living plant (e.g., plant growing in a hot house, kept alive with water, and/or the like). The UV radiation can be used to reduce various infections of the item 56A or plant 56B. If the item 56A or plant 56B is contained within a closed enclosure, the system 20 (FIG. 3) can be configured to turn off the UV radiation source 12 if the enclosure is not fully enclosed.

When UV radiation is emitted within an enclosure, temperature effects of the UV radiation also can be a concern. In order to operate properly, the system 10 (FIG. 3) must be protected from overheating. In an embodiment shown in FIG. 9, to avoid overheating, the computer system 20 can use temporal control 44D to adjust and control distribution of the UV radiation so that the UV radiation applied to items 56 within the storage area 54 is in pulses. The computer system 20 can utilize a time delay between pulses to: cool one or more components of the system 10, the items 56, and/or the enclosure; allow for the onset of a chemical reaction (e.g., one involving a catalyst); signal the completion of the chemical modification; and/or the like. Similarly, the computer system 20 can use the pulsed UV radiation to heat one or more components of the system 10, the items 56, and/or the enclosure; initiate a chemical reaction; and/or the like. In an embodiment, the computer system 20 can cause the UV radiation source 12 to generate pulsed UV radiation for use in conjunction with moving items 56, such as items 56 located on a conveyor belt, and/or the like. In this case, the pulsed UV radiation can be timed with the arrival of the item 56 within a target location. In an embodiment, the pulsed UV radiation can also be correlated with pulsed application of gases, chemicals, and/or the like, to be delivered in an area. Still further, the computer system 20 can use pulsed UV radiation to analyze time resolved fluorescence of the item 56.

As described herein, embodiments can be implemented as part of any of various types of storage systems. FIGS. 4A-4C show illustrative storage devices for use with an ultraviolet radiation system 10 (FIG. 1) according to embodiments. For example, the storage device can be a refrigerator and/or freezer (FIG. 4A) for storing a plurality of food items. Alternatively, the storage device can be a cooler (FIG. 4B). The storage device can be a pantry (FIG. 4C, e.g., a shelf in the pantry), and/or the like. In each case, an embodiment of the system 10 can be implemented in conjunction therewith using any solution. To this extent, it is understood that embodiments of the system 10 can vary significantly in the number of devices, the size of the devices, the power requirements for the system, and/or the like. Regardless, it is understood that these are only exemplary storage devices and that the system 10 may be applicable to other storage devices not specifically mentioned herein.

Figure 5:
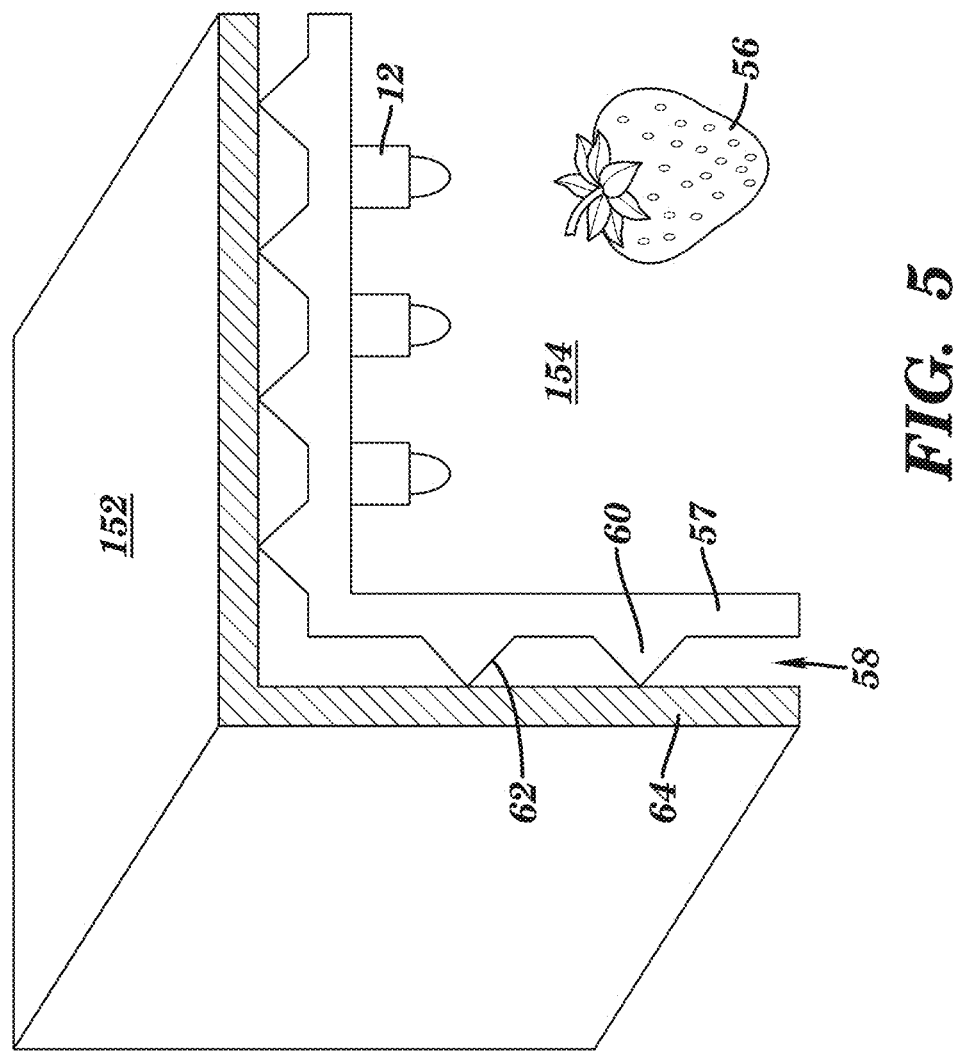
FIG. 5 shows a partial cross-sectional perspective view of an illustrative storage device according to an embodiment.

In an embodiment, the ultraviolet radiation source 12 can include a plurality of ultraviolet light emitters located in various locations adjacent to a storage area. To this extent, FIG. 5 shows a partial cross-sectional perspective view of an illustrative storage device 152 according to an embodiment. The storage device 152 includes a storage area 154 for containing at least one item 56. As shown in the figure, a plurality of ultraviolet radiation emitters 12 are located within the storage area 154. The storage device 152 can be comprised of multiple layers. The layers can protect other storage areas and/or components of the storage device 152 from ultraviolet radiation and/or increase the efficiency of the ultraviolet radiation within the storage area 154. The layers do not allow UV radiation to escape from the storage area 154. The layers of the storage device 152 can include UV absorbing, UV reflective, and/or UV partially reflective material.

For example, an ultraviolet transparent wall 57 can surround the storage area 154 within which the ultraviolet radiation emitters 12 are located. A hollow region 58 can be located between the ultraviolet transparent wall 57 and a highly reflective wall 64. The highly reflective wall 64 can reflect and/or absorb the UV radiation. The highly reflective wall can include a reflectivity of more than approximately 50% as measured for the UV radiation at the normal incidence direction. Approximately 20% of the volume of the hollow region 58 can include a refractive index lower than that of the ultraviolet transparent wall 57. A plurality of elements 60 can protrude from the ultraviolet transparent wall 57 into the hollow region 58. The plurality of elements 60 can include high/low index interfaces 62. During operation, once the ultraviolet radiation emitters 12 shine ultraviolet light into the storage area 154, the high/low index interfaces 60 and the highly reflective wall 64 reflect ultraviolet light back into the storage area 154. The ultraviolet transparent wall 57 can be made of one or more materials that allow ultraviolet radiation to pass through, such as fused silica, an amorphous fluoroplastic (e.g., Teflon by Dupont), and/or the like. Other illustrative materials include alumina sol-gel glass, alumina aerogel, sapphire, aluminum nitride (e.g., single crystal aluminum nitride), boron nitride (e.g., single crystal boron nitride), and/or the like. The outer reflective wall 64 can be made of one or more materials that reflects ultraviolet radiation, such as polished aluminum, a highly ultraviolet reflective expanding polytetrafluoroethylene (ePTFE) membrane (e.g., GORE® Diffuse Reflector Material), and/or the like.

FIGS. 6A and 6B show a perspective view of illustrative storage devices 252 according to other embodiments. In this case, each storage device 252 is shown as having a cylindrical shape. The cylindrical shape for the storage device 252 can allow for increased reflectivity of ultraviolet radiation back into the storage area 254 and onto the stored items from various sides/angles. Furthermore, the cylindrical shape can increase the surface area of items 56 that are exposed to ultraviolet radiation. The cylindrical shaped storage device 252 can be utilized to store, for example, medium sized round food items, such as apples, tomatoes, and/or the like. However, it is understood that the storage device 252 can include any shape and size. The storage device 252 in FIGS. 6A and 6B includes a sliding door 70 for access to the storage area within which items 56 may be located.

A computer system 20 (FIG. 1) can be configured to control the ultraviolet radiation sources 12, such that when sliding door 70 is opened, the ultraviolet radiation sources 12 are turned off. Once sliding door 70 is closed, the ultraviolet radiation sources 12 are turned back on. Although not shown, the storage device 252 may also include an inner ultraviolet radiation transparent enclosure and an outer ultraviolet radiation reflective wall, as shown and described herein. Furthermore, the storage device 252 can include a shelf 72 for the items 56. In an embodiment, the shelf 72 is formed of an ultraviolet radiation transparent material so that the items 56 located on the shelf 72 can be subjected to ultraviolet radiation from any direction.

Figure 7:
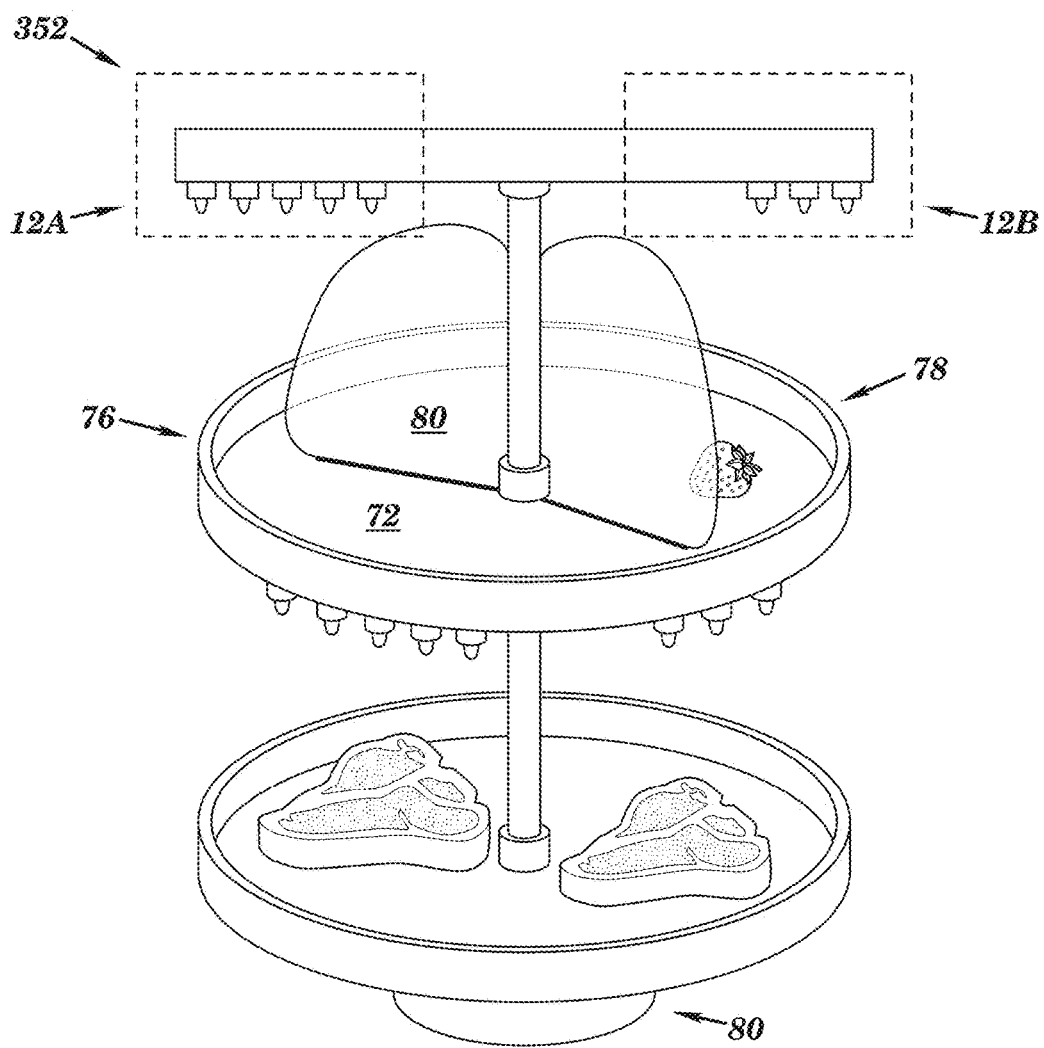
FIG. 7 shows a perspective view of an illustrative storage device according to an embodiment.

FIG. 7 shows a perspective view of an illustrative storage device 352 according to an embodiment. In this embodiment, the storage device 352 can include a plurality of sub-compartments that are individually/separately monitored by the computer system 20 (FIG. 1) using the feedback component 14 (FIG. 1). It is understood that the plurality of sub-compartments can be located within an inner ultraviolet radiation transparent enclosure, such as the enclosure 57 shown in FIG. 5. Furthermore, the ultraviolet radiation sources 12 in each sub-compartment can be individually controlled by the computer system 20. For example, a shelf 72 can be partitioned into a first sub-compartment 76 and a second sub-compartment 78, which are separated by a divider 80. The divider 80 can include a material that is transparent to visible and/or infrared light, but absorbing to UV radiation, so that the UV radiation in one sub-compartment does not enter another sub-compartment. Each of the plurality of sub-compartments 76, 78 can include the same type of UV sources 12.

Alternatively, as shown in FIG. 7, the first sub-compartment 76 can include a first type of UV source 12A, and the second sub-compartment 78 can include a second type of UV source 12B. The computer system 20 can control the UV sources 12A, 12B, such that the first sub-compartment 76 is subjected to a first operating configuration and the second sub-compartment 78 is subjected to a second operating configuration. The particular operating configuration for each sub-compartment can differ. Furthermore, the computer system 20 can control the UV source 12A to emit radiation having a first set of attributes (e.g., intensity, wavelength, temporal distribution, and spatial distribution) and control the UV source 12B to emit radiation having a second set of attributes (e.g., intensity, wavelength, temporal distribution, and spatial distribution). Any combination of one or more of the second set of attributes can be different from the first set of attributes. For example, the UV source 12A can include a full intensity, while the UV source 12B includes a zero intensity. Conversely, the UV source 12A can include a zero intensity, while the UV source 12B includes a full intensity. Furthermore, the computer system 20 can independently tune the relative intensities of each UV source 12A, 12B, and either UV source 12A, 12B can have any intensity between zero and full. Similarly, the computer system 20 can independently adjust the wavelength, temporal and/or spatial distributions, and/or the like of the UV sources 12A, 12B.

Additionally, the shelves 72 may revolve, e.g., via a motor (not shown). The motor may be controlled by the computer system 20 and rotate according to a timing schedule, such that the first sub-compartment 76 and the second sub-compartment 78 each receive ultraviolet light emitted by one of the UV sources 12A, 12B according to a particular operating configuration at a specific time. Although UV sources 12A, 12B are shown as mounted above the shelf 72, it is understood that UV sources can also be within the shelf 72, below the shelf 72, and/or the like.

Returning to FIG. 3, it is understood that the system 10 may include a power component 19 that is implemented separately from the storage device 52 to supply power to one or more of the various components of system 10, such as ultraviolet radiation sources 12, motor 80 (FIG. 10), feedback component 14, computer system 20, and/or the like. For example, the storage device 52 may comprise a cooler or the like, which does not include or otherwise require any power source. Furthermore, the storage device 52 may comprise a power source that is insufficient to operate the various devices of system 10 in addition to maintaining one or more aspects of the environment within the storage area 54 for a desired period of time. Regardless, the power component 19 can be utilized to operate system 10. The power component 19 can comprise any source of power including, but not limited to, the power grid, a battery set, an automotive charger, a solar cell, and/or the like. In an embodiment, the computer system 20 can implement multiple modes of operation depending on the source of power. In particular, when a power component 19 of limited capacity is being utilized, one or more functions of system 10 can be disabled and/or reduced to lengthen an operating time for system 10. For example, use of ultraviolet radiation source 12 to prolong the life of items within the storage area 54 or disinfect the storage area 54 by generating a higher intensity of ultraviolet radiation can be disabled.

An environment within the storage area 54 can be controlled by an environmental control component 18. In an illustrative implementation, the environmental control component 18 can comprise a temperature control module, a humidity control module, and/or a convection control module. During normal operation of the environmental control component 18, a user 6 (FIG. 1) (e.g., using external interface component 26B) can select a desired temperature, humidity, and/or the like, to maintain within storage area 54. The environmental control component 18 can subsequently operate one or more cooling/heating components of temperature control module to maintain the desired temperature, operate one or more humidifying/dehumidifying components of humidity control module to maintain the desired humidity, operate one or more air or fluid convection components (e.g., fan, pump, vent, valve, etc.) of convection control module to assist in maintaining a relatively even temperature/humidity within storage area 54, and/or the like. Alternatively, local temperature control within storage area 54 can be maintained by cool air recirculation that is controlled by the environmental control component 18.

The computer system 20 can be configured to adjust one or more operating parameters of the environmental control component 18 based on a set of current conditions in the storage area 54 and/or an operating configuration of the UV radiation source 12. For example, the computer system 20 can adjust one or more of: a temperature, a humidity, a gas convection, and/or a fluid convection of the storage area 54 in response to a set of biological activity dynamics and/or according to a currently selected operating configuration. To this extent, each operating configuration can further define a set of target environmental conditions for use during the UV illumination. Such environmental conditions can include a target temperature, a target humidity, additional illumination by non-ultraviolet sources (e.g., visible, infrared), air circulation, and/or the like. Furthermore, one or more of the environmental conditions can change over time during implementation of the operating configuration. In an illustrative embodiment, the computer system 20 can operate the environmental control component 18 to circulate air into the chamber 55, e.g., during implementation of the ethylene decomposition operating configuration. Furthermore, the set of current conditions in the storage area 54 can include an operating condition of one or more components of the system 10, such as the ultraviolet radiation source(s) 12. Information regarding the operating condition can be used to, for example, notify a user 6 of a problem using the alarm component 23, alter one or more aspects of an operating configuration, and/or the like. Additionally, the set of current conditions in the storage area 54 can include data corresponding to a dose of ultraviolet radiation delivered by an ultraviolet radiation source 12 during a predetermined time period. In this case, the computer system 20 can dynamically determine when to turn off the ultraviolet radiation source 12.

It is understood that the set of current conditions in the storage area 54 can include one or more attributes corresponding to a set of biological activity dynamics present within the storage area. The set of biological activity dynamics can include, for example, a presence of biological activity (e.g., exponential bacterial growth), a location of the biological activity, a type of biological activity (e.g., type of organism), a concentration of the biological activity, an estimated amount of time an organism has been in a growth phase (e.g., exponential growth and/or stationary), and/or the like. The set of biological activity dynamics can include information on the variation of the biological activity over time, such as a growth rate, a rate with which an area including the biological activity is spreading, and/or the like. In an embodiment, the set of biological activity dynamics are related to various attributes of bacteria activity within an area, including, for example, the presence of detectable bacteria activity, measured bacteria population/concentration time dynamics, growth phase, and/or the like. Additionally, as described herein, the storage area 54 can include catalysts for enhancing the suppression of the biological activity. For example, the storage area 54 can include titanium dioxide, $TiO_2$.

As described herein, aspects of the invention can be implemented to treat (e.g., preserve, disinfect, and/or the like) various types of food stored in various types of environments. A typical environment can comprise a refrigerated environment, in which food is frequently stored to extend the shelf life of the food. However, embodiments can be implemented in other non-refrigerated environments, in which food is stored for a period of time, e.g., to ripen, prior to being used, and/or the like. Furthermore, an embodiment can be implemented in conjunction with a freezer, in which the temperature is maintained well below the freezing point of water. To this extent, the types of food items to which aspects of the invention can be implemented can include various types of food as described herein. As described herein, the foods can include various types of fruits and vegetables. However, the foods also can include frozen consumables, such as ice cubes, ice cream, and/or the like. Furthermore, the foods can include liquids, grains, cereals, and/or the like. Additionally, as described herein, embodiments can be implemented to treat non-food items stored in any type of environment. Such non-food items can include, for example, frozen/liquid chemicals, sand, wood, and/or the like. Regardless, it is understood that a treated item can be ultraviolet transparent (e.g., semi-transparent), ultraviolet absorbing, and/or ultraviolet reflective.

In an embodiment, the computer system 20 can be configured to operate the UV radiation source 12 (e.g., during the storage life preservation operating configuration 50A) to generate ultraviolet radiation to, for example, maintain and/or increase natural phenols, including one or more types of flavonoids, in the food items 56 within the storage area 54. In this case, the computer system 20 can increase the nutritional qualities, including antioxidant benefits, and/or increase storage life of the food items 56.

Figure 10:
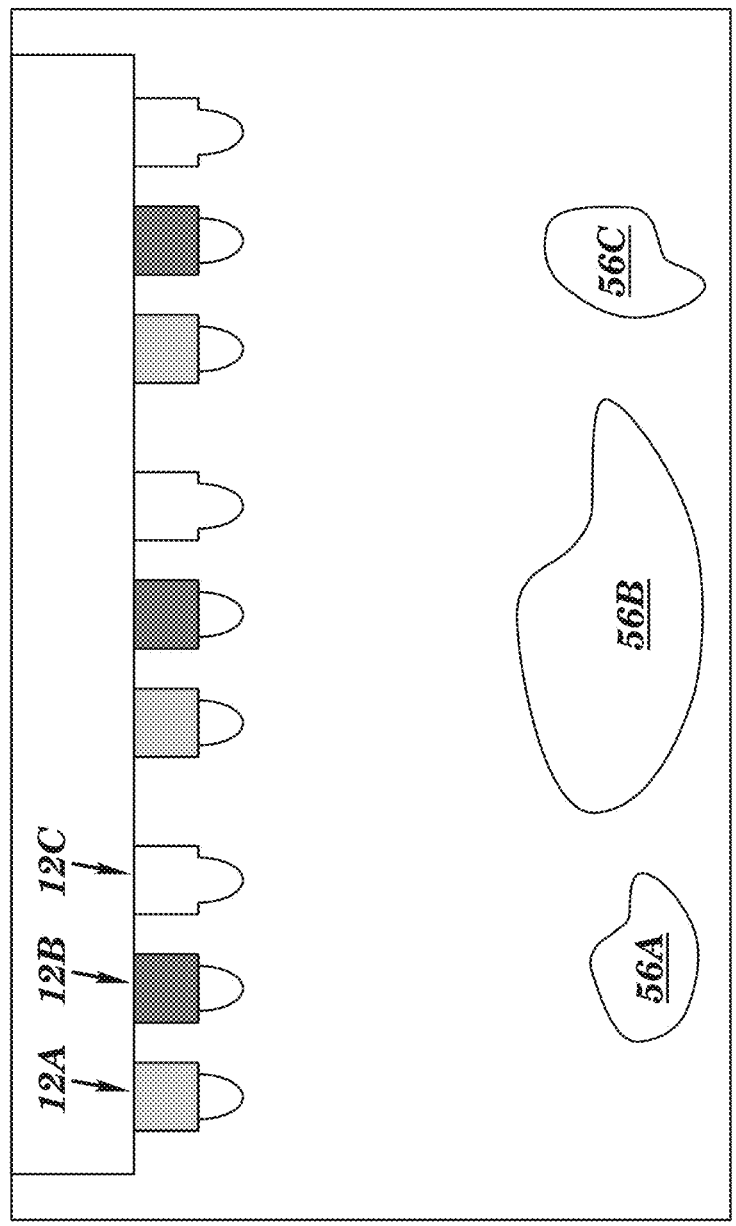
FIG. 10 shows a partial cross-sectional view of an illustrative storage device according to an embodiment.

Turning now to FIG. 10, an embodiment of the system 10 (FIG. 1) can include a plurality of radiation sources (e.g., UV and/or other radiation) that the computer system 20 (FIG. 1) can operate under different control parameters. For example, the system 10 can include a set of first UV radiation sources 12A, a set of second UV radiation sources 12B, and a set of third UV radiation sources 12C. In an illustrative embodiment, the computer system 20 can operate the first set of UV radiation sources 12A to generate UV radiation at approximately 250 nanometers, the second set of UV radiation sources 12B to generate UV radiation at approximately 275 nanometers, and the third set of UV radiation sources 12C to generate radiation at approximately 310 nanometers. It is understood that this is only illustrative, and the system 10 additional and/or alternative UV radiation sources operating at shorter and/or longer wavelengths. Furthermore, the different wavelengths can have different intensity values, depending on a desired effect on the corresponding set of items 56A-56C. For example, in an ethylene decomposition operating configuration, the computer system 20 can operate the UV radiation sources 12A-12C to emit UV radiation between approximately 285 nanometers and 305 nanometers. If ethylene is detected, the computer system 20 can activate these wavelengths with higher intensity to eliminate the buildup of the ethylene gas.

Figure 11:
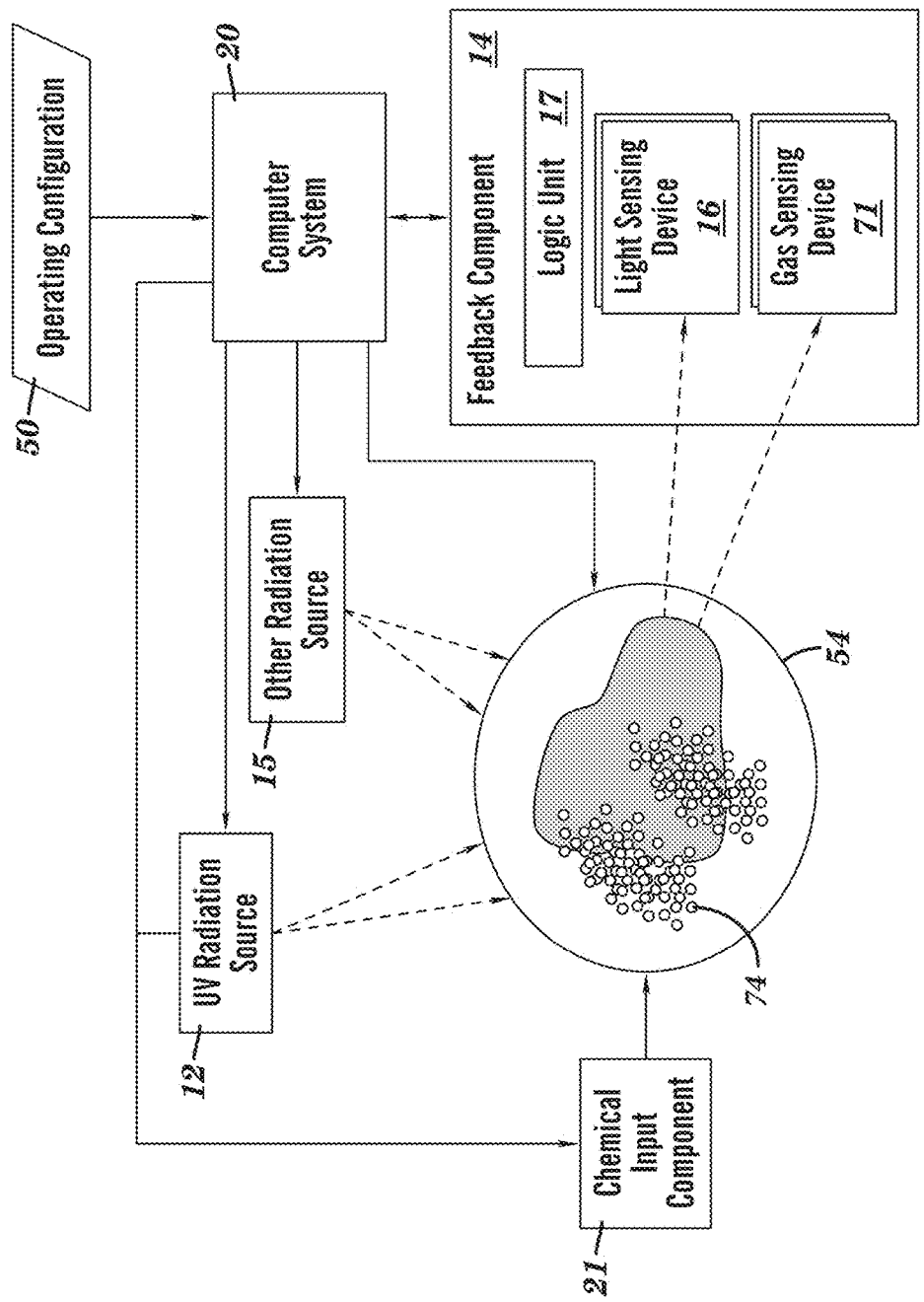
FIG. 11 shows an illustrative system including an ultraviolet radiation system according to an embodiment.

In any embodiment described herein, chemical gases or catalysts can be introduced and involved in photochemical reactions to elicit desired effects on item(s) 56. For example, turning now to FIG. 11, the computer system 20 can operate a chemical input component 21 to introduce chemical gases and catalysts into the storage area 54. The chemicals deposited by the chemical input component 21 can be in the gas, liquid, and/or solid phase. For example, titanium oxide ($TiO_2$) 74 can be used to create a photocatalytic oxidation. These chemicals can be added to the storage area 54 containing the item 56, and can be a result of the chemical reaction that occurred within the storage area 54. Furthermore, the feedback component 14 can include a gas sensing device 71 capable of detecting a presence of a target gas within the storage area 54. In another embodiment, catalytic converters can be deposited to increase the rate of chemical reactions within the storage area 54.

In any embodiment described herein, the computer system 20 can adjust the control parameters for the UV and/or other radiation sources in order to achieve a desired effect on an item. It is understood that achievement of a desired effect may not be exact or perfect and some acceptable error between the real outcome and the desired effect may be present. A magnitude of the acceptable error is dependent upon the desired effect and the corresponding application.

Returning to FIG. 3, a system 10 described herein can be used to disinfect tissue, destroy DNA molecules, increase vitamin levels of a target item 56 (e.g., a human and/or an animal), and/or the like. In this case, the UV-induced mutations in the DNA of micro-organisms do not inactivate their metabolic function, such as respiration and enzymatic activities, nor kill the micro-organisms. Many micro-organisms have enzyme systems that repair UV-induced damage. Ambient radiation in the range of approximately 300 nanometers and approximately 500 nanometers can expedite such repair mechanism and is referred to as photo-repair. In order to eliminate the effect of photo-repair, the computer system 20 can adjust an intensity of the ultraviolet radiation source 12 based on a target ambient level of radiation in the wavelength range of approximately 300 nanometers to approximately 500 nanometers. In this embodiment, the feedback component 14 can be configured to detect the ambient radiation in a wavelength range of approximately 300 nanometers to approximately 500 nanometers. For example, the sensing devices 16 of the feedback component 14 can include detectors with a peak sensitivity to radiation within this ambient radiation range. It is understood that ambient radiation is any radiation in the range of approximately 300 nanometers to approximately 500 nanometers that exists when the UV sources 12 are turned off.

The computer system 20 can control and/or adjust the radiation emitted by the UV radiation source 12 according to an adjustment algorithm based on the feedback data regarding ambient radiation. In an embodiment, an adjustment algorithm can be constructed through a number of experimental tests where the inactivation process is measured. To this extent, the adjustment algorithm can be constructed based on experimental measurements of DNA repair rates due to the particular ambient radiation wavelength detected. For example, the adjustment algorithm can be obtained by obtaining data regarding an effect of the UV radiation 13 on the item 56 without the presence of the ambient radiation and then the effect of the UV radiation 13 on the item 56 with the presence of the ambient radiation. Subsequently, the computer system 20 can control and adjust the UV source 12 so that the desired effect on the item 56 is still obtained in the presence of ambient radiation. It is understood, however that it might be beneficial to irradiate the target item 56 by different frequencies at different times. For example, disinfection of target item 56 can require irradiation frequencies that consist of UVC, whereas food and plant preservation can require UVB and/or UVA radiation. For this particular situation, UVC radiation can be applied first for a set duration of time followed by application of UVB and UVA radiation.

While shown and described herein as a method and system for managing a storage area, it is understood that aspects of the invention further provide various alternative embodiments. For example, in one embodiment, the invention provides a computer program fixed in at least one computer-readable medium, which when executed, enables a computer system to manage the storage area using a process described herein. To this extent, the computer-readable medium includes program code, such as the analysis program 30 (FIG. 1), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the analysis program 30 (FIG. 1), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for managing the storage area. In this case, the generating can include configuring a computer system, such as the computer system 20 (FIG. 1), to implement a method of managing the storage area as described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
a plurality of layers forming a storage area configured to contain a set of items, wherein the plurality of layers include an outer ultraviolet reflective layer, an inner ultraviolet transparent layer, and a layer located between the outer ultraviolet reflective layer and the inner ultraviolet transparent layer, wherein a refractive index of the layer located between the outer ultraviolet reflective layer and the inner ultraviolet transparent layer is lower than a refractive index of the inner ultraviolet transparent layer;
a set of ultraviolet radiation sources configured to generate ultraviolet radiation directed at the set of items within the storage area; and
a monitoring and control system configured to:
monitor a set of current conditions of at least one of: the storage area or the set of items located in the storage area; and
control the ultraviolet radiation generated by the set of ultraviolet radiation sources using the set of current conditions and a target effect for the set of items by adjusting at least one of: an intensity, a wavelength, a temporal distribution, or a spatial distribution of the ultraviolet radiation.

2. The system of claim 1, wherein the layer comprises a hollow region.

3. The system of claim 1, wherein the outer ultraviolet reflective layer is at least 50% reflective.

4. The system of claim 1, wherein the inner ultraviolet transparent layer includes a plurality of protrusions extending into the layer between the outer ultraviolet reflective layer and the inner ultraviolet transparent layer.

5. The system of claim 1, wherein the controlling includes adjusting the spatial distribution of the ultraviolet radiation by directing the ultraviolet radiation source at at least a portion of the set of items within the storage area.

6. The system of claim 1, wherein the outer ultraviolet reflective layer comprises a material chosen from a group consisting of: aluminum and ePTFE.

7. The system of claim 1, further comprising a set of ultraviolet transparent shelves located within the storage area.

8. The system of claim 1, wherein the inner ultraviolet transparent layer comprises a material chosen from a group consisting of: fused silica, fluoroplastic, alumina sol-gel, aerogel, and sapphire.

9. The system of claim 1, wherein a peak wavelength range for the ultraviolet radiation is between 275 nanometers and 280 nanometers.

10. The system of claim 1, wherein a peak wavelength range for the ultraviolet radiation is between 290 nanometers and 295 nanometers.

11. The system of claim 1, further comprising:
a set of visible light sources configured to generate visible light directed within the storage area; and
at least one visible camera configured to detect the visible light within the storage area.

12. A system comprising:
a plurality of layers forming a storage area configured to contain a set of items, wherein the plurality of layers include an outer ultraviolet reflective layer, an inner ultraviolet transparent layer, and a layer located between the outer ultraviolet reflective layer and the inner ultraviolet transparent layer, wherein a refractive index of the layer located between the outer ultraviolet reflective layer and the inner ultraviolet transparent layer is lower than a refractive index of the inner ultraviolet transparent layer;
a component configured to control at least one environmental condition of the storage area, wherein the at least one environmental condition includes at least one of: a temperature, a humidity, a gas convection, or a fluid convection;
a set of ultraviolet radiation sources configured to generate ultraviolet radiation directed at the set of items within the storage area; and
a monitoring and control system configured to:
monitor a set of current conditions of at least one of: the storage area or the set of items located in the storage area; and
control the ultraviolet radiation generated by the set of ultraviolet radiation sources using the set of current conditions and a target effect for the set of items by adjusting at least one of: an intensity, a wavelength, a temporal distribution, or a spatial distribution of the ultraviolet radiation.

13. The system of claim 12, wherein controlling the ultraviolet radiation includes:
pulsing the ultraviolet radiation; and
measuring, using a fluorescence sensor, a time resolved fluorescence between each pulse of the ultraviolet radiation.

14. The system of claim 13, further comprising at least one visible light sensor configured to detect visible light within the storage area.

15. The system of claim 14, wherein at least one item in the set of items is a plant.

16. A refrigeration device comprising:
a plurality of layers forming a storage area configured to contain a set of items, wherein the plurality of layers include an outer ultraviolet reflective layer, an inner ultraviolet transparent layer, and a hollow layer located between the outer ultraviolet reflective layer and the inner ultraviolet transparent layer, wherein a refractive index of the hollow layer located between the outer ultraviolet reflective layer and the inner ultraviolet transparent layer is lower than a refractive index of the inner ultraviolet transparent layer;
a component configured to control at least one environmental condition of the storage area, wherein the at least one environmental condition includes at least one of: a temperature, a humidity, a gas convection, or a fluid convection;
a set of ultraviolet radiation sources configured to generate ultraviolet radiation directed at the set of items within the storage area; and
a monitoring and control system configured to:
monitor a set of current conditions of at least one of: the storage area or the set of items located in the storage area; and
control the ultraviolet radiation generated by the set of ultraviolet radiation sources using the set of current conditions and a target effect for the set of items by adjusting at least one of: an intensity, a wavelength, a temporal distribution, or a spatial distribution of the ultraviolet radiation.

17. The device of claim 16, wherein the outer ultraviolet reflective layer is at least 50% reflective.

18. The device of claim 16, wherein the set of current conditions includes a temperature of a surface of the set of items, and wherein the controlling includes adjusting the temporal distribution of the ultraviolet radiation so that the ultraviolet radiation directed at the set of items is in pulses, wherein the pulsed ultraviolet radiation allows time for at least one of: cooling the set of items, heating the set of items, allowing an onset of a chemical reaction, and initiating a chemical reaction.

19. The device of claim 16, wherein the inner ultraviolet transparent layer includes a plurality of protrusions extending into the layer between the outer ultraviolet reflective layer and the inner ultraviolet transparent layer.

20. The device of claim 16, further comprising a set of ultraviolet transparent shelves located within the storage area.

* * * * *